(12) United States Patent
Deutsch

(10) Patent No.: US 8,808,226 B2
(45) Date of Patent: Aug. 19, 2014

(54) DEVICE AND METHOD FOR IRRIGATING-EVACUATING A BODY CAVITY

(75) Inventor: Israel Deutsch, Petach-Tikva (IL)

(73) Assignee: Hospitech Respiration Ltd., Petach-Tikva (IL)

( * ) Notice: Subject to any disclaimer, the term of this patent is extended or adjusted under 35 U.S.C. 154(b) by 0 days.

(21) Appl. No.: 13/342,125

(22) Filed: Jan. 2, 2012

(65) Prior Publication Data
US 2012/0090620 A1  Apr. 19, 2012

Related U.S. Application Data

(63) Continuation-in-part of application No. PCT/IL2011/000520, filed on Jun. 29, 2011.

(60) Provisional application No. 61/406,201, filed on Oct. 25, 2010, provisional application No. 61/359,404, filed on Jun. 29, 2010.

(51) Int. Cl.
- *A61M 1/00* (2006.01)
- *A61M 5/178* (2006.01)
- *A61M 16/00* (2006.01)

(52) U.S. Cl.
USPC ............................ 604/36; 604/27; 128/207.14

(58) Field of Classification Search
USPC .................... 128/207.14–207.17; 604/27–45, 604/118–121
See application file for complete search history.

(56) References Cited

U.S. PATENT DOCUMENTS

| | | | |
|---|---|---|---|
| 4,260,077 A * | 4/1981 | Schroeder | 222/137 |
| 4,457,747 A | 7/1984 | Tu | |
| 4,857,056 A * | 8/1989 | Talonn | 604/135 |
| 4,909,783 A * | 3/1990 | Morrison | 604/30 |
| 5,050,297 A | 9/1991 | Metzger | |
| 5,235,973 A | 8/1993 | Levinson | |
| 5,254,086 A * | 10/1993 | Palmer et al. | 604/38 |
| 5,429,610 A * | 7/1995 | Vaillancourt | 604/191 |
| 5,655,518 A | 8/1997 | Burden | |
| 5,743,886 A * | 4/1998 | Lynn et al. | 604/191 |
| 5,819,723 A * | 10/1998 | Joseph | 128/207.14 |

(Continued)

FOREIGN PATENT DOCUMENTS

| | | |
|---|---|---|
| EP | 2305343 | 4/2011 |
| WO | WO 92/07602 | 5/1992 |

(Continued)

OTHER PUBLICATIONS

Qosina "Male Luer Lock Alternating Procedure Syringe, 10ml, Transparent Blue", Component Information, Qosina 2012 Print Catalog, p. 390, 2012.

(Continued)

*Primary Examiner* — Justine Yu
*Assistant Examiner* — Valerie L Skorupa

(57) ABSTRACT

A device for irrigating a body cavity is disclosed. The device comprises a first pump and a second pump being operatively linked via a manually-operated actuator member. The actuator member has at least a mode in which the actuator member activates the first pump to eject an initial volume of fluid out of the device, and a mode in which the actuator member activates the second pump to eject fluid out of the device and simultaneously activates the first pump to withdraw fluid into the device.

34 Claims, 34 Drawing Sheets

(56) References Cited

U.S. PATENT DOCUMENTS

| | | | |
|---|---|---|---|
| 5,890,488 | A | 4/1999 | Burden |
| 5,957,883 | A | 9/1999 | Lin |
| 6,168,568 | B1 | 1/2001 | Gavriely |
| 6,261,238 | B1 | 7/2001 | Gavriely |
| 6,383,142 | B1 | 5/2002 | Gavriely |
| 6,390,091 | B1 | 5/2002 | Banner et al. |
| 6,571,796 | B2 | 6/2003 | Banner et al. |
| 6,621,278 | B2 | 9/2003 | Ariav |
| 6,641,394 | B2 * | 11/2003 | Garman ........................ 433/81 |
| 6,723,053 | B2 | 4/2004 | Ackerman et al. |
| 6,820,618 | B2 | 11/2004 | Banner et al. |
| 6,843,250 | B2 | 1/2005 | Efrati |
| 6,856,141 | B2 | 2/2005 | Ariav |
| 2001/0021821 | A1 * | 9/2001 | Wang et al. .................. 604/110 |
| 2002/0105340 | A1 | 8/2002 | Ariav |
| 2003/0069549 | A1 * | 4/2003 | MacMahon et al. .......... 604/266 |
| 2004/0104733 | A1 | 6/2004 | Ariav |
| 2004/0207409 | A1 | 10/2004 | Ariav et al. |
| 2005/0027206 | A1 | 2/2005 | Ariav |
| 2005/0027250 | A1 * | 2/2005 | Suresh et al. ................. 604/110 |
| 2005/0277891 | A1 * | 12/2005 | Sibbitt .......................... 604/191 |
| 2007/0089748 | A1 * | 4/2007 | Madsen et al. ........... 128/207.15 |
| 2008/0283052 | A1 * | 11/2008 | Young ..................... 128/200.26 |
| 2009/0038620 | A1 | 2/2009 | Efrati |
| 2009/0229605 | A1 | 9/2009 | Efrati et al. |
| 2010/0319702 | A1 | 12/2010 | Wood et al. |
| 2010/0326446 | A1 | 12/2010 | Behlmaier |
| 2011/0023884 | A1 | 2/2011 | Cuevas et al. |
| 2011/0023889 | A1 | 2/2011 | Lin et al. |
| 2011/0046464 | A1 | 2/2011 | Debreczeny et al. |
| 2011/0073115 | A1 | 3/2011 | Wood et al. |
| 2011/0146690 | A1 | 6/2011 | Wood et al. |

FOREIGN PATENT DOCUMENTS

| | | |
|---|---|---|
| WO | WO 00/67013 | 11/2000 |
| WO | WO 03/036321 | 5/2003 |
| WO | WO 03/048688 | 6/2003 |
| WO | WO 2004/072658 | 8/2004 |
| WO | WO 2005/062719 | 3/2005 |
| WO | WO 2005/076727 | 8/2005 |
| WO | WO 2007/023492 | 3/2007 |
| WO | WO 2010/046874 | 4/2010 |
| WO | WO 2012/001691 | 1/2012 |
| WO | WO 2013/102905 | 7/2013 |

OTHER PUBLICATIONS

International Search Report and the Written Opinion Dated Nov. 30, 2011 From the International Searching Authority Re. Application No. PCT/IL2011/000520.
Wilder et al. "Clinical Evaluation of Tracheal Pressure Estimation From the Endotracheal Tube Cuff Pressure", Journal of Clinical Monitoring and Computing, 14(1): 29-34, 1998.
International Preliminary Report on Patentability Dated Jan. 17, 2013 From the International Bureau of WIPO Re. Application No. PCT/IL2011/000520.
International Search Report and the Written Opinion Dated Apr. 30, 2013 From the International Searching Authority Re. Application No. PCT/IL2013/050015.
Communication Pursuant to Article 94(3) EPC Dated Nov. 28, 2013 From the European Patent Office Re. Application No. 11743640.2.
Notification of Office Action Dated May 6, 2014 From The State Intellectual Property Office of the People's Republic of China Re. Application No. 201180042161.1 and Its Translation Into English.
Search Report Dated May 6, 2014 From the State Intellectual Property Office of the People's Republic of China Re. Application No. 201180042161.1 and Its Translation Into English.

* cited by examiner

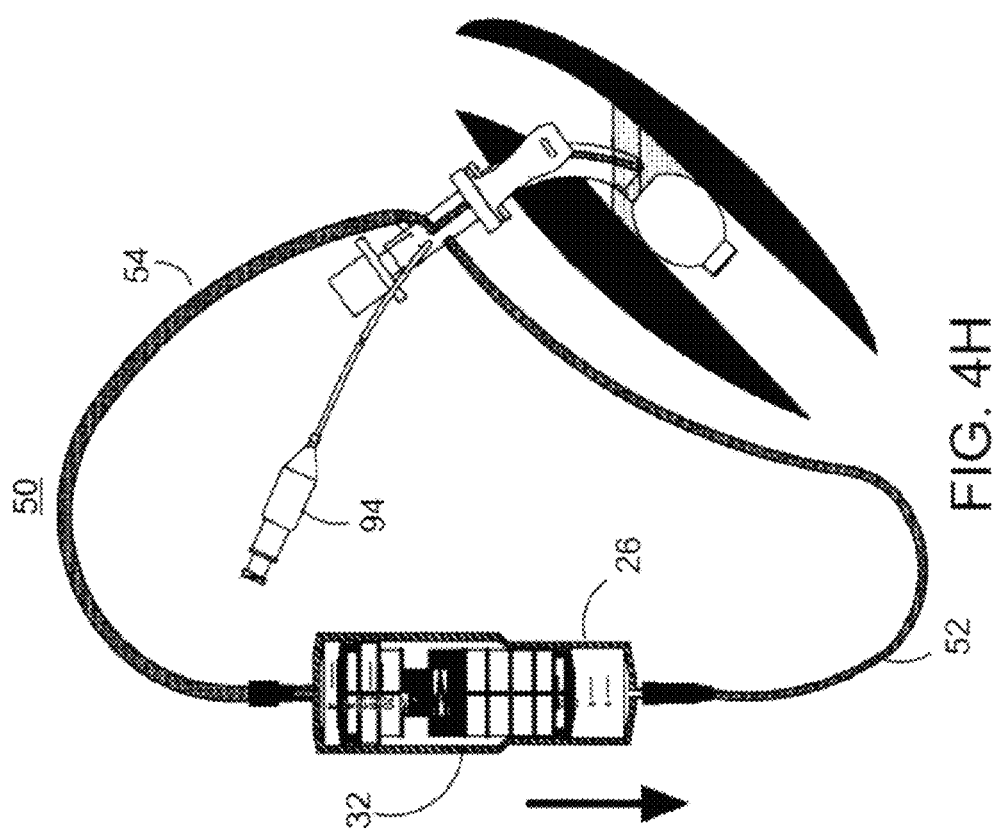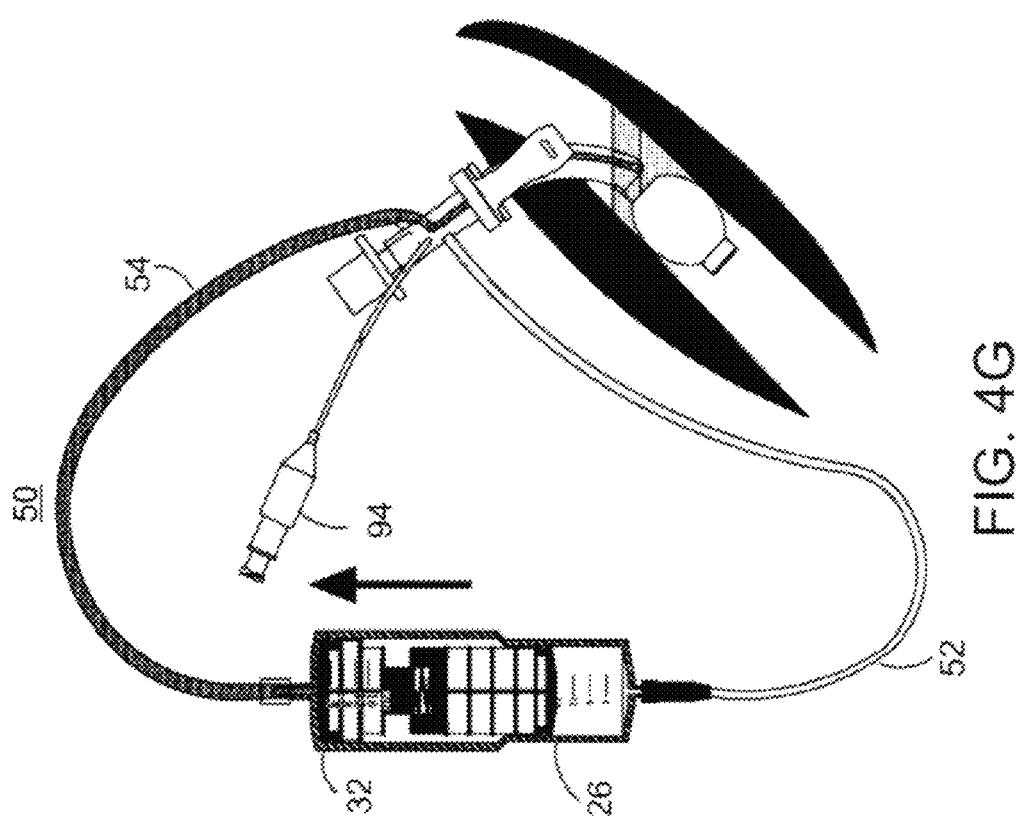

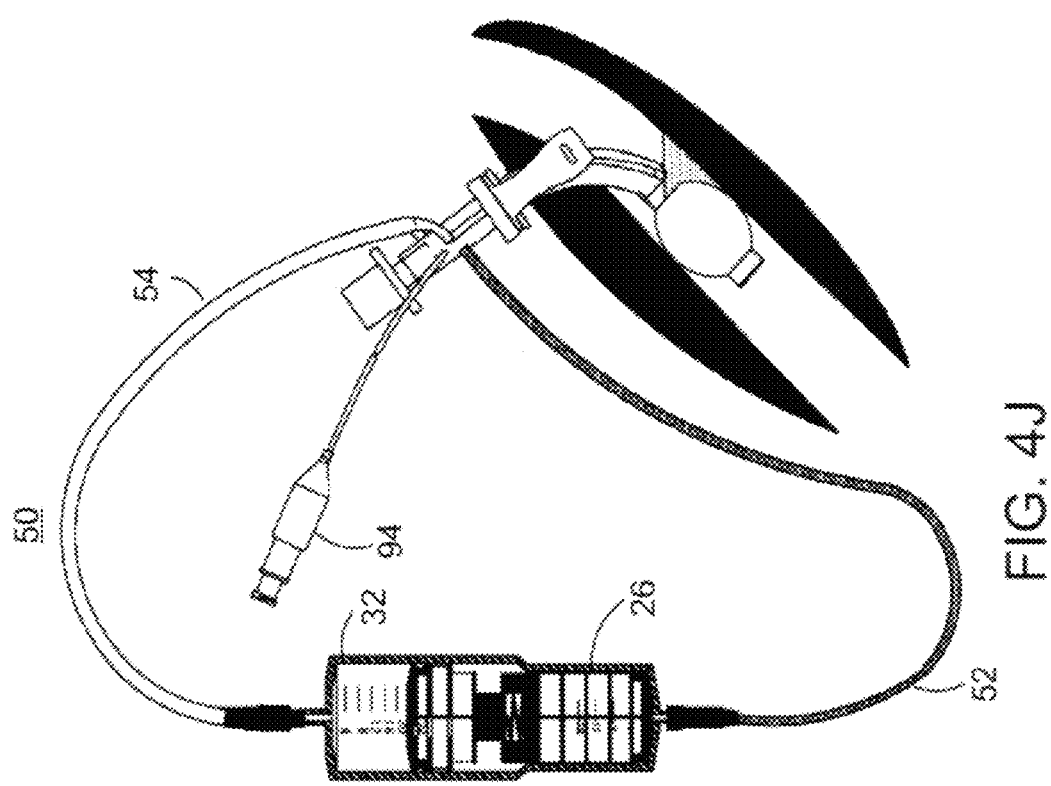
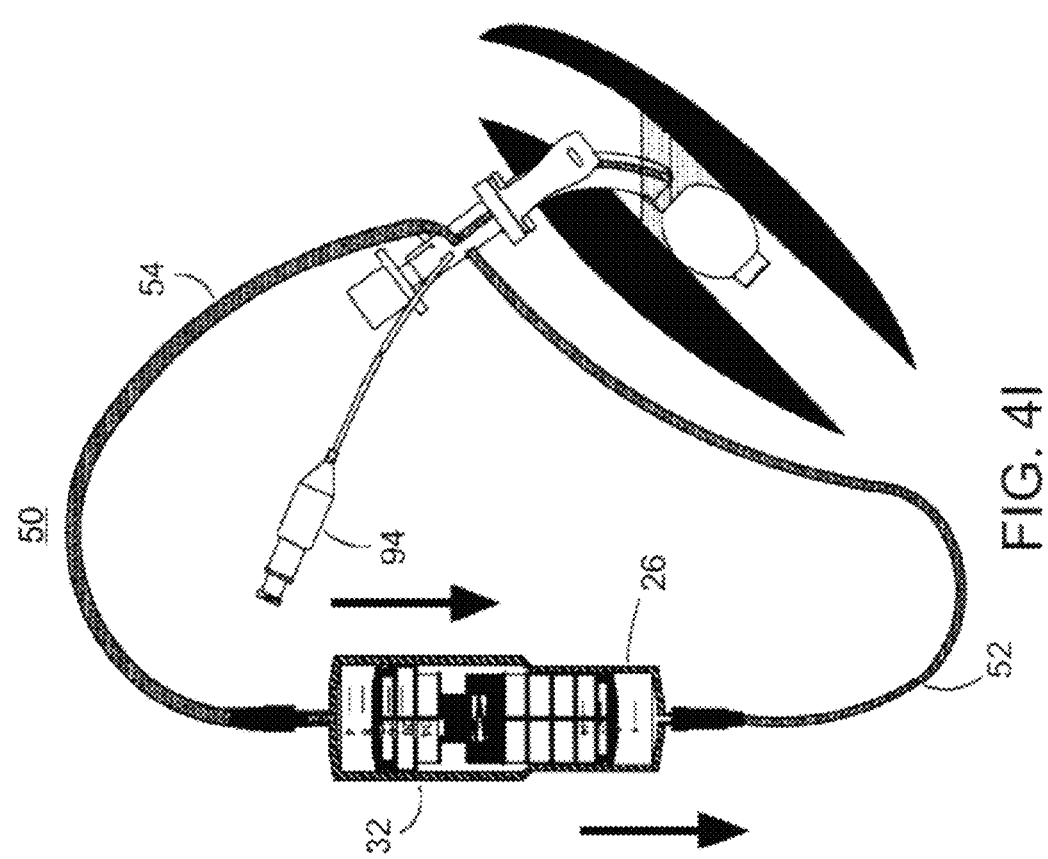

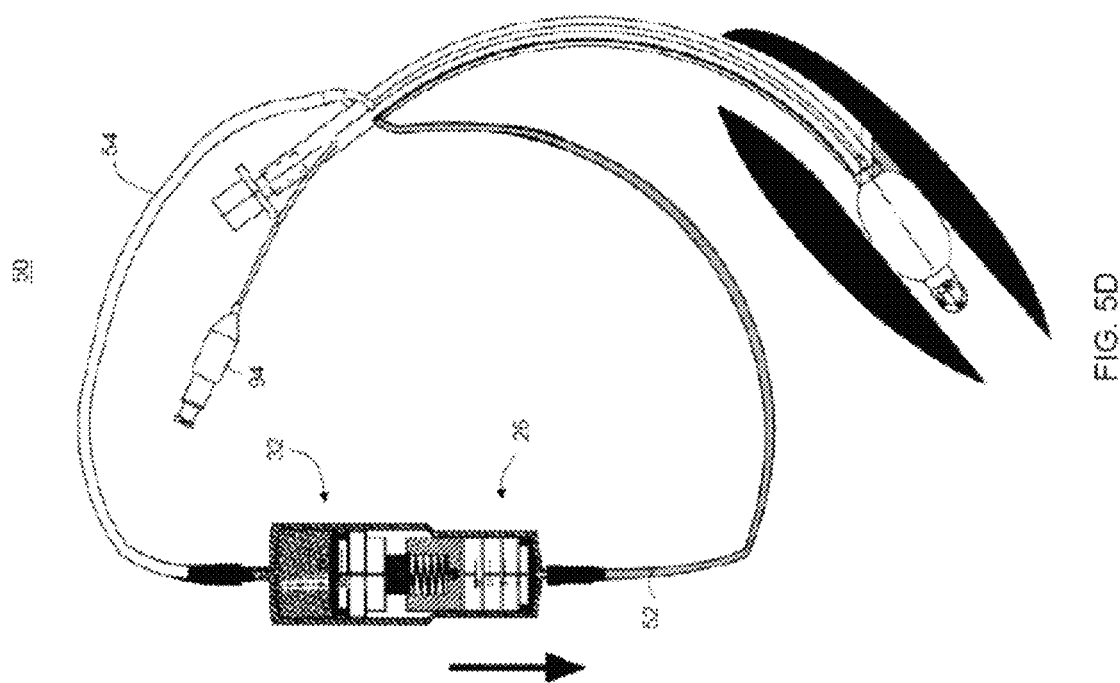
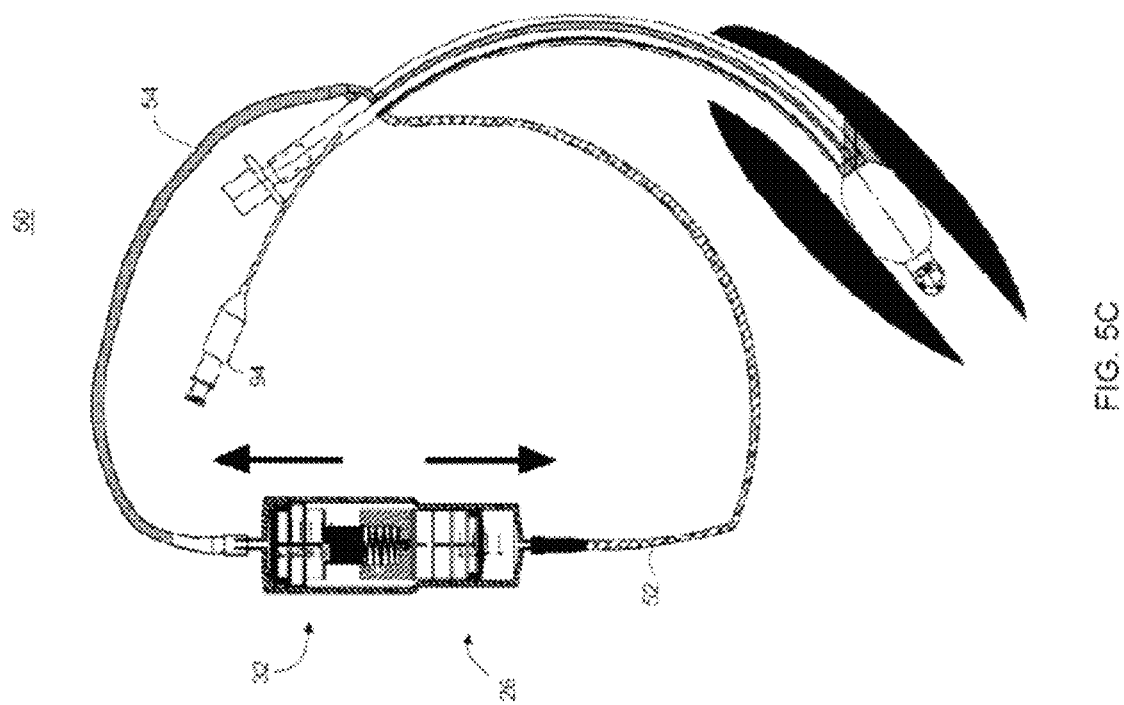

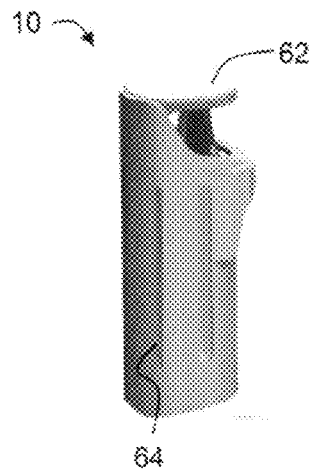
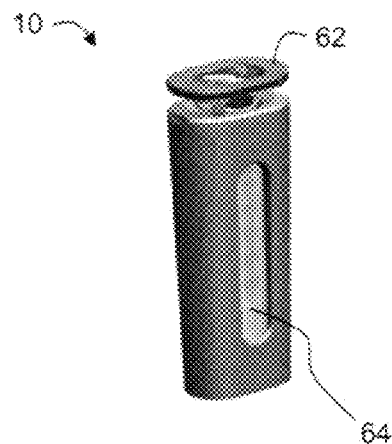
FIG. 6A
FIG. 6B
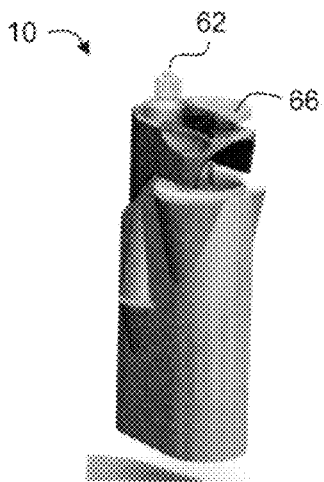
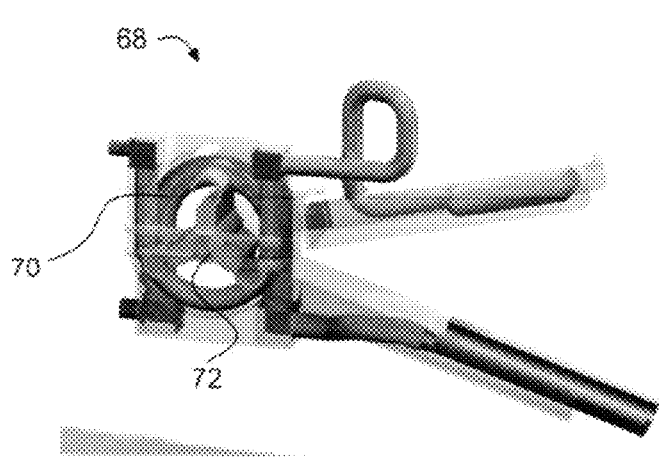
FIG. 6C
FIG. 6D

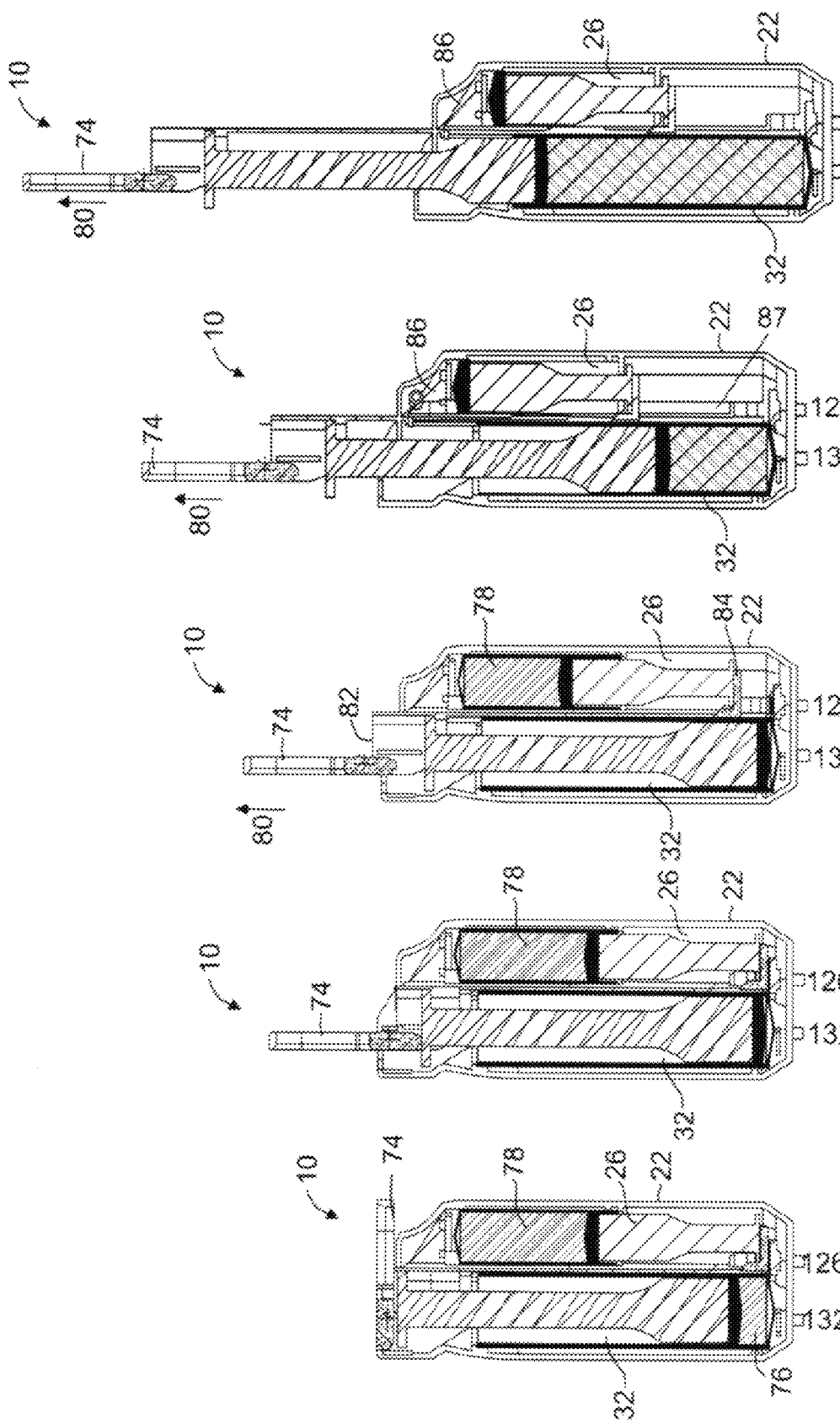

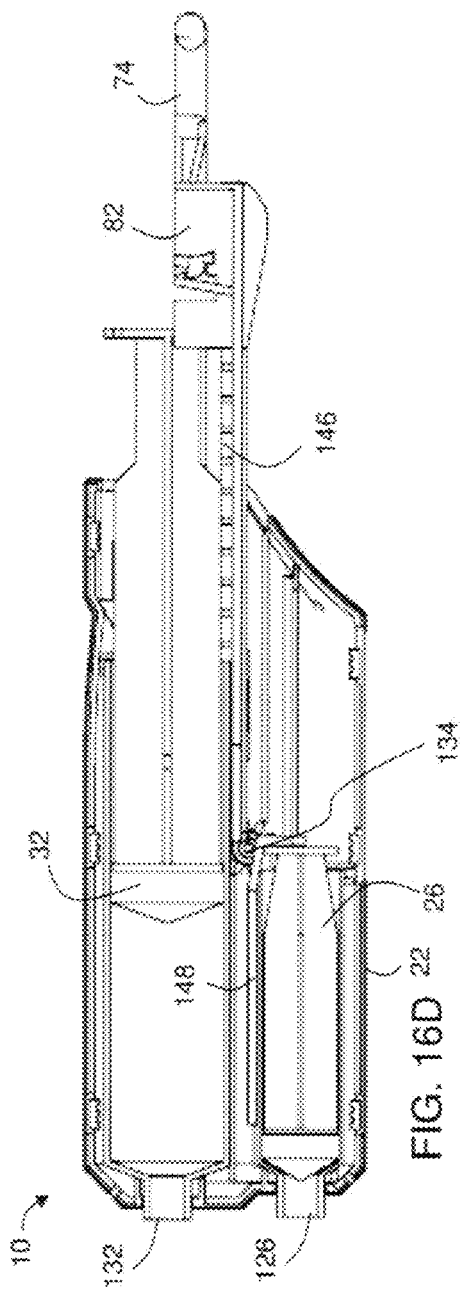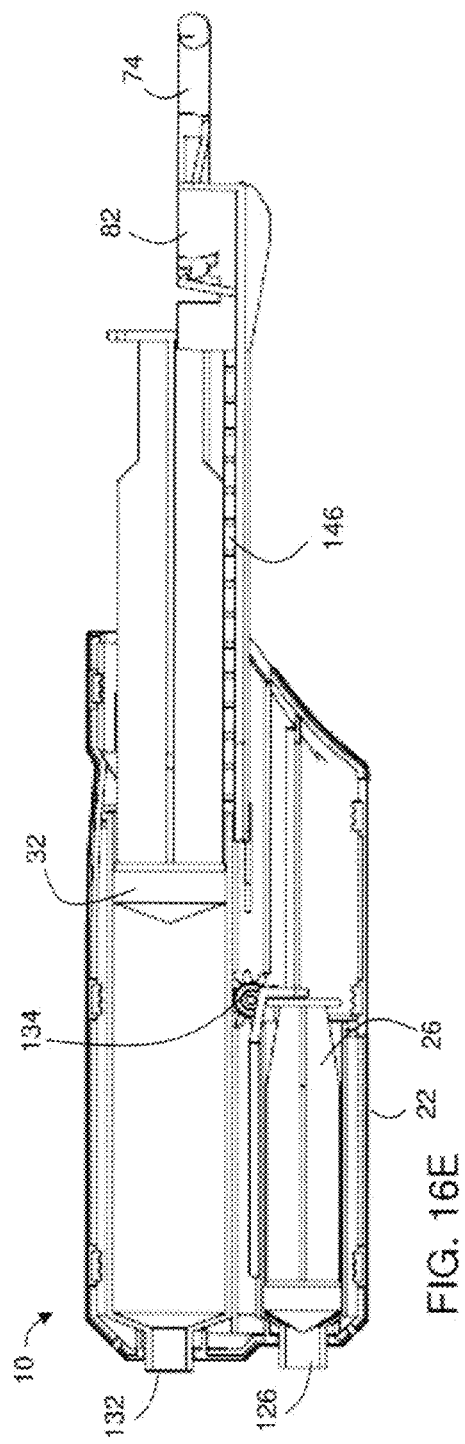

DEVICE AND METHOD FOR IRRIGATING-EVACUATING A BODY CAVITY

RELATED APPLICATIONS

This application is a continuation-in-part (CIP) of International Patent Application No. PCT/IL2011/000520 having International filing date of Jun. 29, 2011, which claims the benefit of priority of U.S. Provisional Patent Application Nos. 61/359,404 filed on Jun. 29, 2010, and 61/406,201 filed on Oct. 25, 2010. The contents of the above applications are all incorporated herein by reference.

FIELD AND BACKGROUND OF THE INVENTION

The present invention, in some embodiments thereof, relates to a hand-held, and optionally manually-operated, device for irrigating-evacuating a body cavity and specifically, but not exclusively, to a manually operated pumps mechanism which can be used to remove secretions from a subglottic region of an intubated subject.

Intubation involves positioning of a tube, such as an endotracheal tube (ETT) or a tracheostomy tube through the trachea of a subject terminating at a position above the carina, anterior to a position between the second and fourth thoracic vertebrate.

Endotracheal intubation is used to mechanically ventilate the subject's lungs when normal breathing is not supported, or to apply anesthetic gases during surgical intervention.

Tracheostomy is an operative procedure that creates a surgical airway in, anterior to a position between the cervical trachea. The resulting stoma can serve independently as an airway or as a site for a tracheostomy tube to be inserted. This tube allows a person to breathe without the use of their nose or mouth, or being mechanically ventilated when hospitalized or in homecare environment.

In order to create enough air pressure to accomplish mechanical ventilation and to prevent escape of gases past the tube, the tubes are sealed against the trachea using, for example, an inflatable cuff.

The inflatable cuff is inflated so as to engage the wall of the trachea and thereby seal the trachea and prevent gases being introduced through the tracheal tube from simply leaking around the tube. While use of an inflatable cuff is important for operability of an ETT, it can also contribute to complications.

Intubated patients can develop pneumonia resulting from an infection of the lungs induced by contaminated, pooled secretions with digestive content bypassing the epiglottis. To overcome these risks, endotracheal and tracheostomy tubes which enable single lumen suction or double lumen irrigation and suction of such secretions have been developed. Single lumen suction tubes are limited in that the suction often causes direct suction to be exerted on the tracheal mucosa which may then result in damage to the mucosa. Double lumen tubes while being vastly superior in enabling clearance of secretions require the use of complicated and expensive irrigation pumps.

U.S. Pat. No. 4,457,747 discloses an exchange transfusion device with two coupled, automatically driven syringes, one in a blood withdrawal system and one in a fresh blood injection system. The coupling insures that the volume of blood removed from a baby in the withdrawal system will be simultaneously replaced by an equal volume of fresh blood from the injection system.

U.S. Pat. No. 4,909,783 discloses an apparatus for maintaining pressure in the eye cavity while simultaneously removing and replacing fluid therein. The apparatus includes two syringes connected via conduits with hollow needles for insertion through a surface of the eye. One of the syringes is adapted to discharge a fluid and the other adapted to draw in a fluid. The Apparatus also includes drive means which displace the plungers of the syringes in opposite directions, whereby equal volumes of fluid are drawn in and discharged to the eye.

U.S. Pat. No. 5,957,883 discloses a synchronous vitreous lavage device for ophthalmology. The device includes a platform, a pair of main supporters, an auxiliary supporter, a pair of gears, a pair of movable seats, a pair of screw rods and a clamp for holding and controlling two lavage syringes. When the handle affixed to the gear is rotated by the turning of the hand, the first screw rod is rotated in one direction and the second screw rod is rotated in the opposite direction. The first movable seat and the second movable seat move in opposite directions. Then, one of the syringes absorbs the bloody water from the eyeball into it, and the other syringe simultaneously injects water into the eyeball. The absorption and injection of the two syringes are synchronously and isovolemicaly.

U.S. Published Application No. 20030069549 discloses a fluid exchange device which includes a first member connected to a piston that propels irrigant fluid and a second member connected to a piston that withdraws aspirant fluid. The members are in fluid communication with lumens that produce a closed loop with a target fluid exchange site within the body. The action of a trigger pulled toward a handle exerts a force on the irrigant piston that forces fluid through an irrigant lumen and simultaneously withdraws the aspirant piston to accomplish the fluid exchange at the target site.

International Publication No. WO1992007602 discloses an endotracheal tube having a double lumen sump action evacuating means associated therewith. The endotracheal tube includes a double lumen evacuating means, which is formed into the walls of the endotracheal tube. The evacuating means terminate at a suction eye positioned above an inflatable cuff for the endotracheal tube.

SUMMARY OF THE INVENTION

According to an aspect of some embodiments of the present invention there is provided a device for irrigating a body cavity with fluid. In various exemplary embodiments of the invention the device is a hand-held device. The device comprises a pump mechanism configured for delivering a first volume of fluid to the body cavity and delivering a second volume of fluid to the body cavity while concomitantly withdrawing at least the second volume of fluid from the body cavity. The pump mechanism is optionally and preferably a manually-operated pump mechanism.

According to some embodiments of the invention the pump mechanism is configured to deliver fluid to the body cavity at a first volumetric flow rate and simultaneously withdraw fluid from the body cavity at a second volumetric flow rate, and wherein there is a linear relation between the first and the second volumetric flow rates.

According to some embodiments of the invention the mechanism comprises a first pump and a second pump each being configured for communicating fluid to and from the body cavity, the first pump and the second pump being operatively linked such that operating the second pump to deliver the second volume of fluid into the body cavity activates the first pump to withdraw the at least the second volume of fluid from the body cavity.

According to some embodiments of the invention the mechanism comprises a first pump and a second pump each being configured for communicating fluid to and from the body cavity, the first pump and the second pump being operatively linked such that operating the first pump to withdraw the at least the second volume of fluid from the body cavity activates the second pump to deliver the second volume of fluid into the body cavity.

According to some embodiments of the invention the first pump is a first piston pump having a first piston, and the second pump is a second piston pump having a second piston. According to some embodiments of the first piston is operatively linked to the second piston.

According to some embodiments of the invention the first piston and the second piston are linked in a manner which enables independent movement of the first piston and the second piston through a preset movement range, and linked movement of the first piston and the second piston beyond the preset movement range.

According to some embodiments of the invention movement of the first piston within the preset movement range delivers a first volume of fluid to the body cavity and further wherein movement of the second piston beyond the preset movement range delivers a second volume of fluid and operates the first piston to withdraw at least the second volume of fluid.

According to some embodiments of the invention the piston pumps are syringes having manually operateable plungers.

According to some embodiments of the invention the device comprises an actuator member having a first mode in which both the pumps are inoperative, and a second mode in which the actuator member activates the first pump to eject an initial volume of fluid out of the device.

According to some embodiments of the invention the actuator member additionally has a third mode in which the actuator member activates the second pump to eject a further initial volume of fluid out of the device.

According to some embodiments of the invention the actuator member additionally has a fourth mode in which the actuator member simultaneously activates the second pump to deliver fluid into the body cavity and the first fluid pump to withdraw fluid from the body cavity.

According to some embodiments of the invention the actuator member additionally has a fifth mode in which the actuator member activates only the first fluid pump to withdraw fluid from the body cavity.

According to some embodiments of the invention the actuator member is a mechanical member.

According to an aspect of some embodiments of the present invention there is provided an intubation system comprising the device described herein, and a tube assembly adapted for being introduced into the body cavity.

According to an aspect of some embodiments of the present invention there is provided a device for irrigating a body cavity with fluid. The device comprises two manually-operated syringes having linked plungers, wherein pushing in a first plunger of a first syringe beyond a predetermined travel distance withdraws a second plunger of a second syringe. According to some embodiments of the invention the two manually-operated syringes are of different volumes and/or plunger stroke length.

According to an aspect of some embodiments of the present invention there is provided a device for irrigating a body cavity with fluid. The device comprises a first pump and a second pump being operatively linked via a manually-operated actuator member, wherein the actuator member has at least a mode in which the actuator member activates the first pump to eject an initial volume of fluid out of the device, and a mode in which the actuator member simultaneously activates the second pump to eject fluid out of the device and the first pump to withdraw fluid into the device.

According to some embodiments of the invention the actuator member additionally has a mode in which the actuator member activates only the first fluid pump to withdraw fluid from the body cavity.

According to some embodiments of the invention the actuator member additionally has a mode in which both the pumps are inoperative.

According to some embodiments of the invention the first pump is configured to withdraw fluid to the body cavity at a first volumetric flow rate and the second pump is configured to withdraw fluid from the body cavity at a second volumetric flow rate, and wherein there is a linear relation between the first and the second volumetric flow rates.

According to some embodiments of the invention the piston pumps are aligned parallel to each other such that a withdrawing direction of the first piston pump is parallel to an ejecting direction of the second piston pump.

According to some embodiments of the invention the device comprises a cogwheel configured for linking between a motion of the actuator member and a motion of the second piston.

According to some embodiments of the invention the device comprises a first linear transmission element connected to the actuator member and configured to move together with the actuator member over a movement range selected such that the cogwheel engages the first linear transmission element over part of the range.

According to some embodiments of the invention the device comprises a second linear transmission element connected to the piston of the second pump, wherein the cogwheel engages the second linear transmission element, such that linear motion of the second linear transmission element is established by rotary motion of the cogwheel.

According to some embodiments of the invention the piston pumps are aligned parallel to each other such that a withdrawing direction of the first piston pump is opposite to an ejecting direction of the second piston pump.

According to some embodiments of the invention at least one of the first and the second pumps is a peristaltic pump.

According to some embodiments of the invention the first pump is a container having an under pressure therein.

According to some embodiments of the invention the second pump is a deformable bag.

According to some embodiments of the invention the device comprises a pressure measuring device.

According to some embodiments of the invention at least one of the first and the second pumps comprises a biomarker therein.

According to an aspect of some embodiments of the present invention there is provided a method of irrigating a body cavity with fluid. The method comprises: (a) manually delivering a first volume of fluid to the body cavity; and (b) manually delivering a second volume of the fluid and simultaneously withdrawing at least the second volume of the fluid from the body cavity.

According to some embodiments of the invention the method is effected by a device which comprises a first pump and a second pump each being configured for communicating fluid to and from the body cavity, the first pump and the second pump being operatively linked such that operating the second pump to deliver the second volume of fluid into the body cavity activates the first pump to withdraw the at least the second volume of fluid from the body cavity.

According to some embodiments of the invention the method is effected by a device which comprises a first pump and a second pump each being configured for communicating fluid to and from the body cavity, the first pump and the second pump being operatively linked such that operating the first pump to withdraw the at least the second volume of fluid from the body cavity activates the second pump to deliver the second volume of fluid into the body cavity According to some embodiments of the invention (a) is effected by operating the second pump to deliver a first volume of fluid to the body cavity.

According to some embodiments of the invention (b) is effected by manually operating the first pump to deliver a second volume of the fluid to the body cavity thereby operating the second pump to withdraw fluid from the body cavity.

According to some embodiments of the invention the method is effected by a device which comprises a first pump and a second pump, the device being connected to the body cavity via a tube having a first line in fluid communication with the first pump and a separate second line in fluid communication with the second pump, wherein the method comprises: operating the second pump to deliver fluid into the second line, so as to at least fill the second line; operating the first pump to deliver fluid into the first line, so as to at least fill the first line; and simultaneously operating the first pump to withdraw fluid from the first line and the second pump to deliver fluid into the second line.

According to some embodiments of the invention the method comprises, subsequently to operation (b), withdrawing fluid from the body cavity without delivering fluid into the body cavity.

According to some embodiments of the invention the method comprises connecting the irrigation device to an intubation device which comprises: a flexible tubular body being adapted for being introduced into the trachea of a subject and having a wall defining a main lumen; and an inflatable cuff associated with the tubular body and arranged to be located at a location in the patient trachea; the wall being embedded with at least: (i) two suction lumens with respective openings above the cuff, the openings being arranged laterally with respect to each other within the wall, (ii) a cuff inflation lumen with opening at the cuff, and (ii) an irrigation lumen with opening above the cuff.

According to some embodiments of the invention the manually delivering the second volume of the fluid is at a first volumetric flow rate, and the simultaneously withdrawing the at least the second volume of the fluid is at a second volumetric flow rate, and wherein there is a linear relation between the first and the second volumetric flow rates.

According to some embodiments of the invention the body cavity is the trachea.

According to some embodiments of the invention the body cavity is the trachea and the method is executed during a procedure selected from the group consisting of oral endotracheal intubation and tracheotomy.

According to some embodiments of the invention the body cavity is selected from the group consisting of the ear canal and the intestines.

According to an aspect of some embodiments of the present invention there is provided a kit, comprising the device as described herein, and an intubation device adapted for being introduced into the body cavity, wherein each of the first and the second pumps is connectable to a separate fluid line of the intubation device.

According to some embodiments of the invention the intubation device comprises: a flexible tubular body being adapted for being introduced into the trachea of a subject and having a wall defining a main lumen; and an inflatable cuff associated with the tubular body and arranged to be located at a location in the patient trachea; the tubular body wall being embedded with at least: (i) two suction lumens with respective openings above the cuff, the openings being arranged laterally with respect to each other within the wall, (ii) a cuff inflation lumen with opening at the cuff, and (ii) an irrigation lumen with opening above the cuff.

According to some embodiments of the invention the wall has a dorsal section and a ventral section at opposite sides of a longitudinal axis of the tubular body, wherein the openings of the suction lumens are both located at the dorsal section.

According to some embodiments of the invention the wall has a dorsal section and a ventral section at opposite sides of a longitudinal axis of the tubular body, wherein the opening of the irrigation lumen is located at the ventral section. Preferably, the openings of the suction lumens are separated by a an azimuthal angle which is less than a with respect to the center of a cross-section perpendicular to the longitudinal axis, where $\alpha$ is less than 100° or less than 90° or less than 80° or less than 70° or less than 60° or less than 50° or less than 40° or less than 30° or less than 20°. According to some embodiments of the invention the opening of the irrigation lumen is located at the ventral section. According to some embodiments of the invention the opening of the suction lumens are located at the dorsal section having openings with ducts on the sidereal to enlarge suction ports.

According to some embodiments of the invention the suction lumens embedded in tubular wall are unified to a single fluid line external to the tubular body.

According to some embodiments of the invention the tubular body is adapted for oral endotracheal intubation. According to some embodiments of the invention the tubular body is adapted for tracheostomy intubation.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings and images. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-D are schematic illustrations of the stages of operation of a device, according to some embodiments of the present invention.

FIGS. 2A-E are schematic illustrations of the stages of operation a device in embodiments in which the device is connected to an endotracheal tube.

FIGS. 2F-J are schematic illustrations of the stages of operation a device in embodiments in which the device is connected to a tracheostomy tube.

Figure 3A:
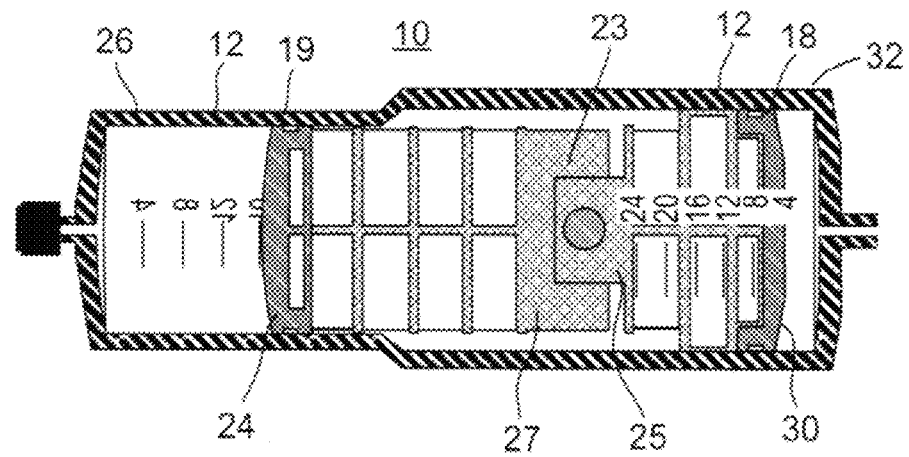
Figure 3B:
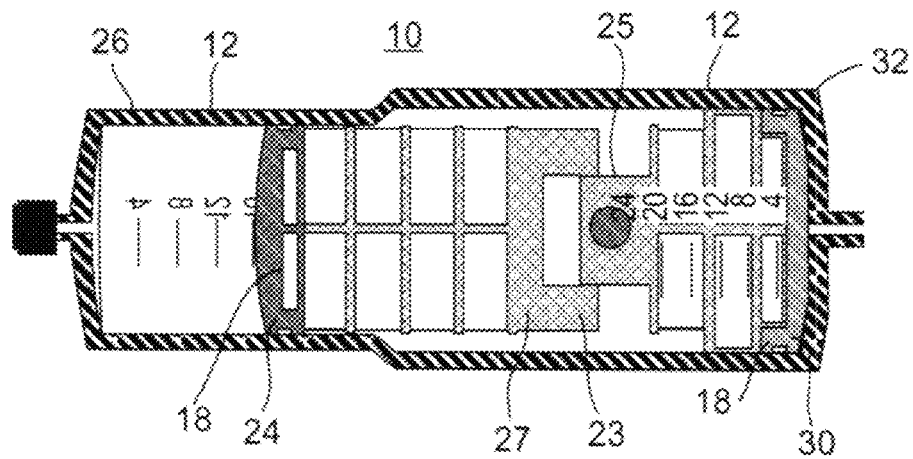
Figure 3C:
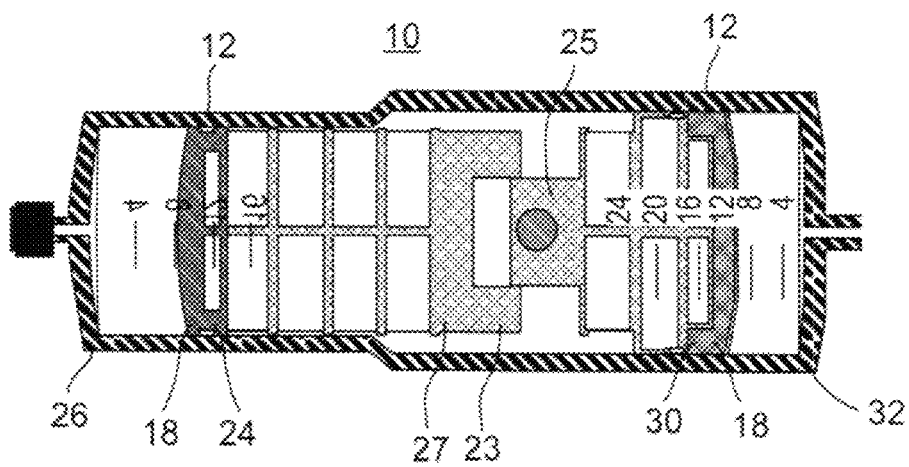

FIGS. 3A-C are schematic illustrations of the stages of operation of a device, specifically showing different barrel and plunger diameters, according to some embodiments of the present invention.

FIGS. 4A-E are schematic illustrations of the stages of operation of the device in embodiments in which the present device is attached to an endotracheal tube and a unidirectional spring is employed.

FIGS. 4F-J are schematic illustrations of the stages of operation of the device in embodiments in which the present device is attached to a tracheostomy tube and a unidirectional spring is employed.

FIGS. 5A-D are schematic illustrations of the stages of operation of an embodiment in which the present device is attached to an endotracheal tube and a bidirectional spring is employed.

FIGS. 5E-H are schematic illustrations of the stages of operation of an embodiment in which the present device is attached to a tracheostomy tube and a bidirectional spring is employed.

FIGS. 6A-G are schematic illustrations of pump mechanisms, according to some embodiments of the present invention.

FIGS. 7A-E are schematic illustrations of a device in embodiments of the invention in which the device comprises an actuator member.

Figure 8A:
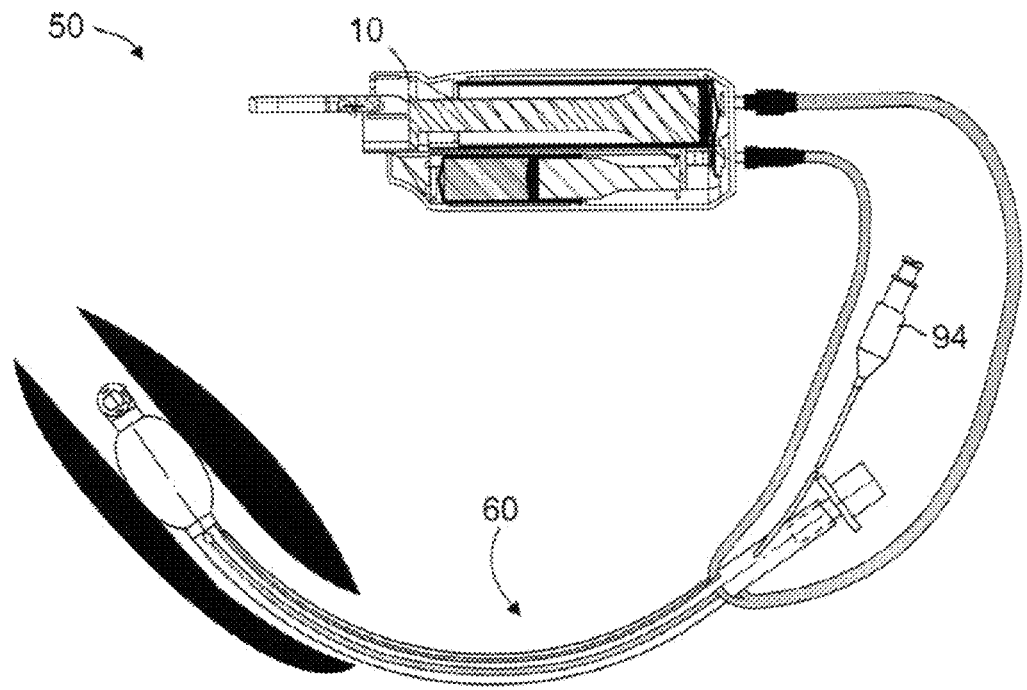
Figure 8B:
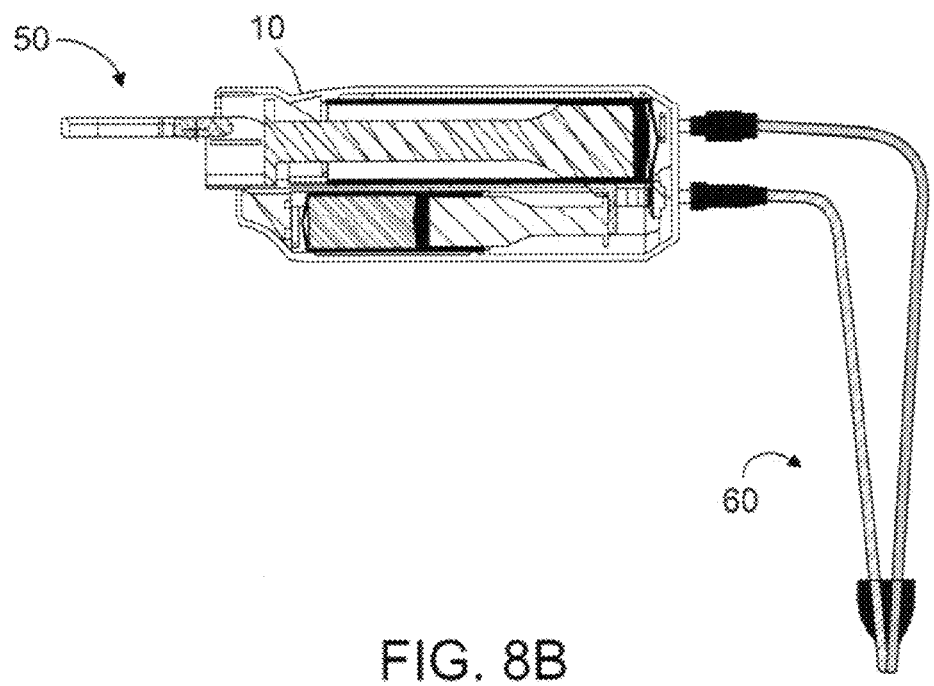

FIGS. 8A and 8B are schematic illustration of a system which comprises a device that including an actuator member and a tube.

Figure 9A:
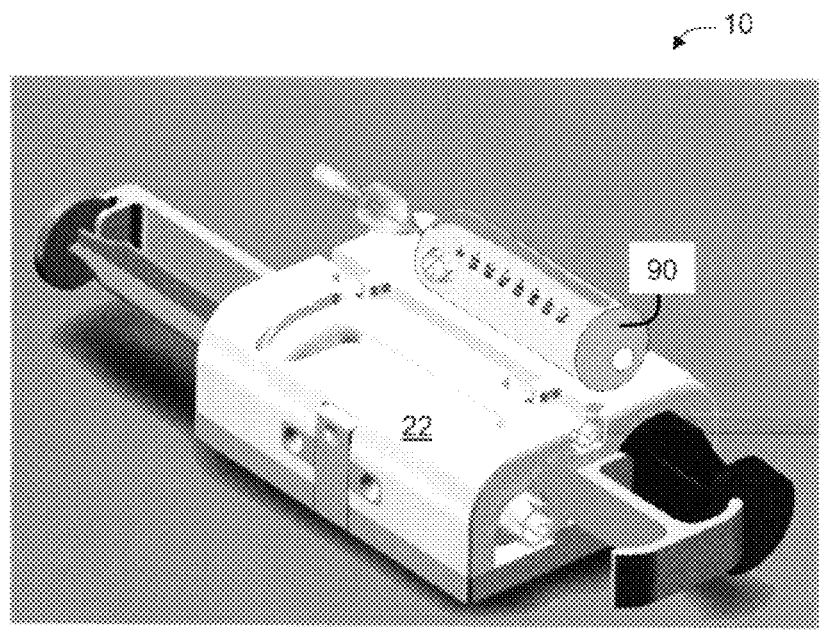
Figure 9B:
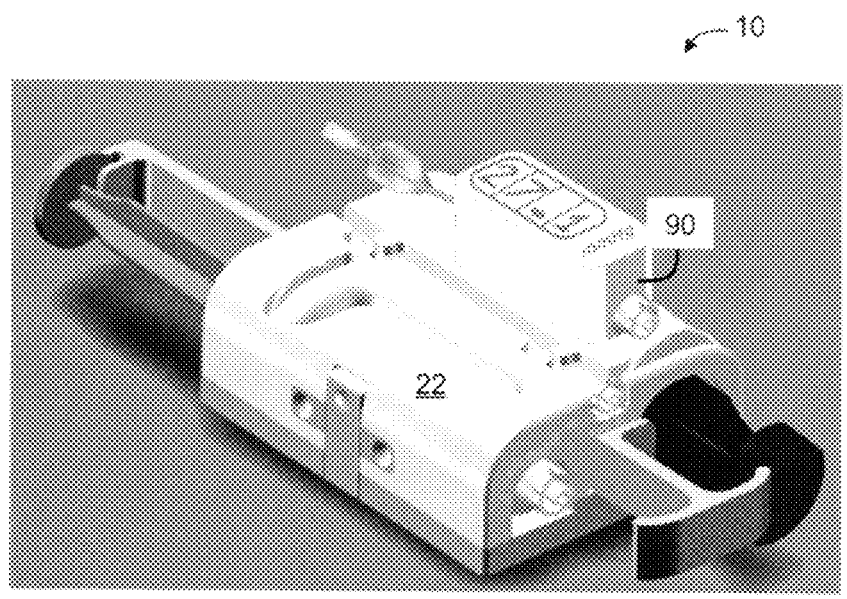

FIGS. 9A and 9B are schematic illustrations of a device in embodiments of the invention in which the device comprises a pressure measuring device.

Figure 10:
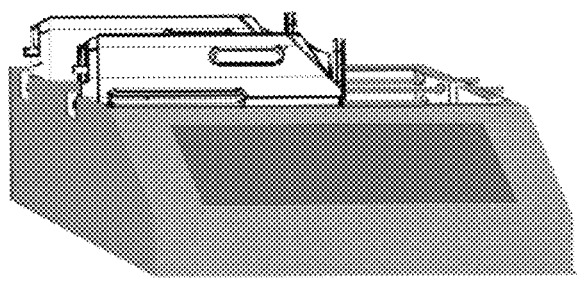

FIG. 10 is a schematic illustration of a pack including two devices, according to some embodiments of the present invention.

Figure 11A:
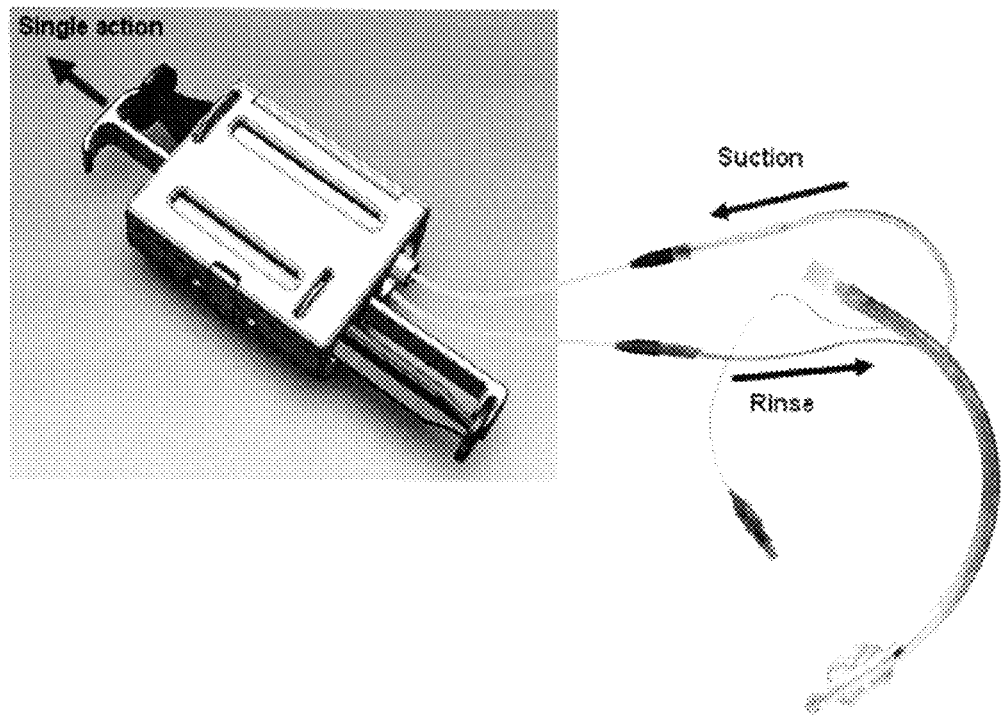
Figure 11B:
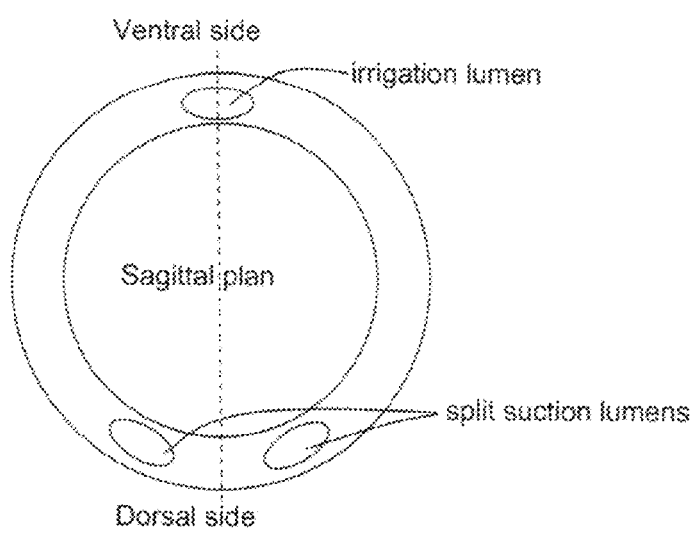

FIGS. 11A-B are schematic illustrations and an image of a device and an endotracheal tube, used in experiments performed according to some embodiments of the present invention.

Figure 12:
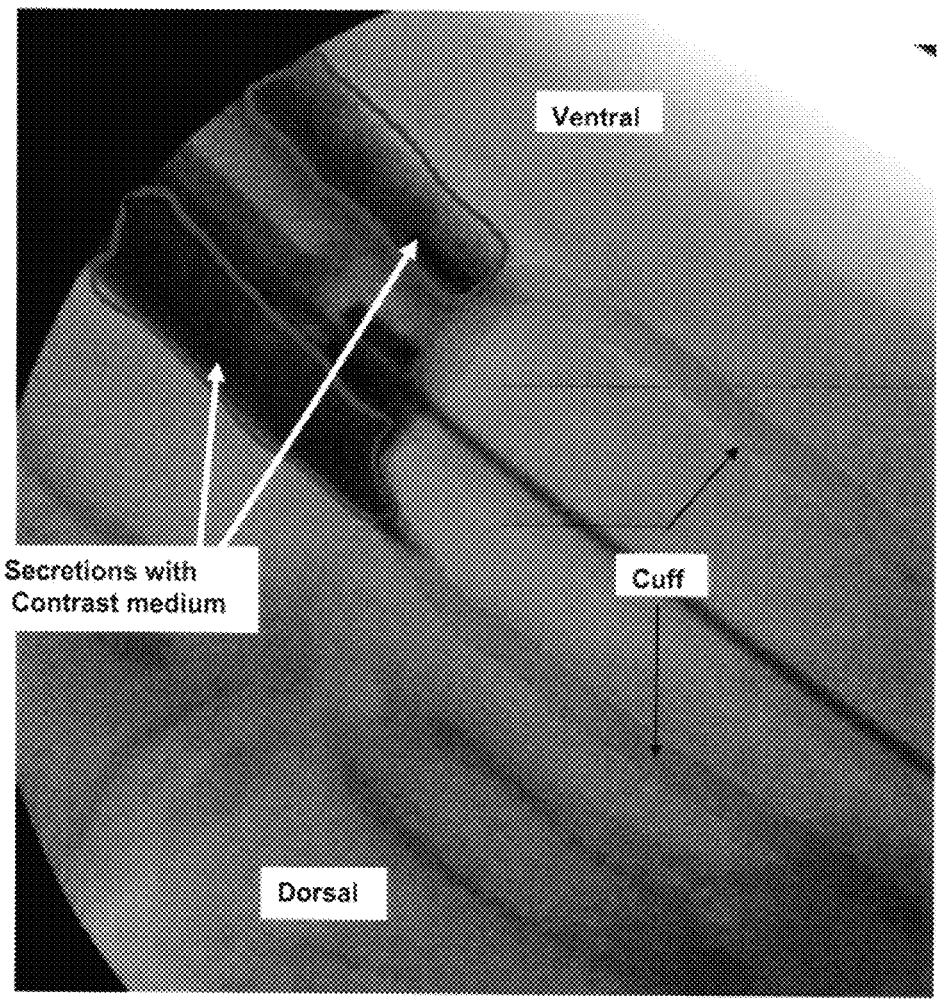

FIG. 12 is a fluoroscopy image of a goat's trachea with the endotracheal tube of the present embodiments before evacuation of the secretions.

Figure 13:
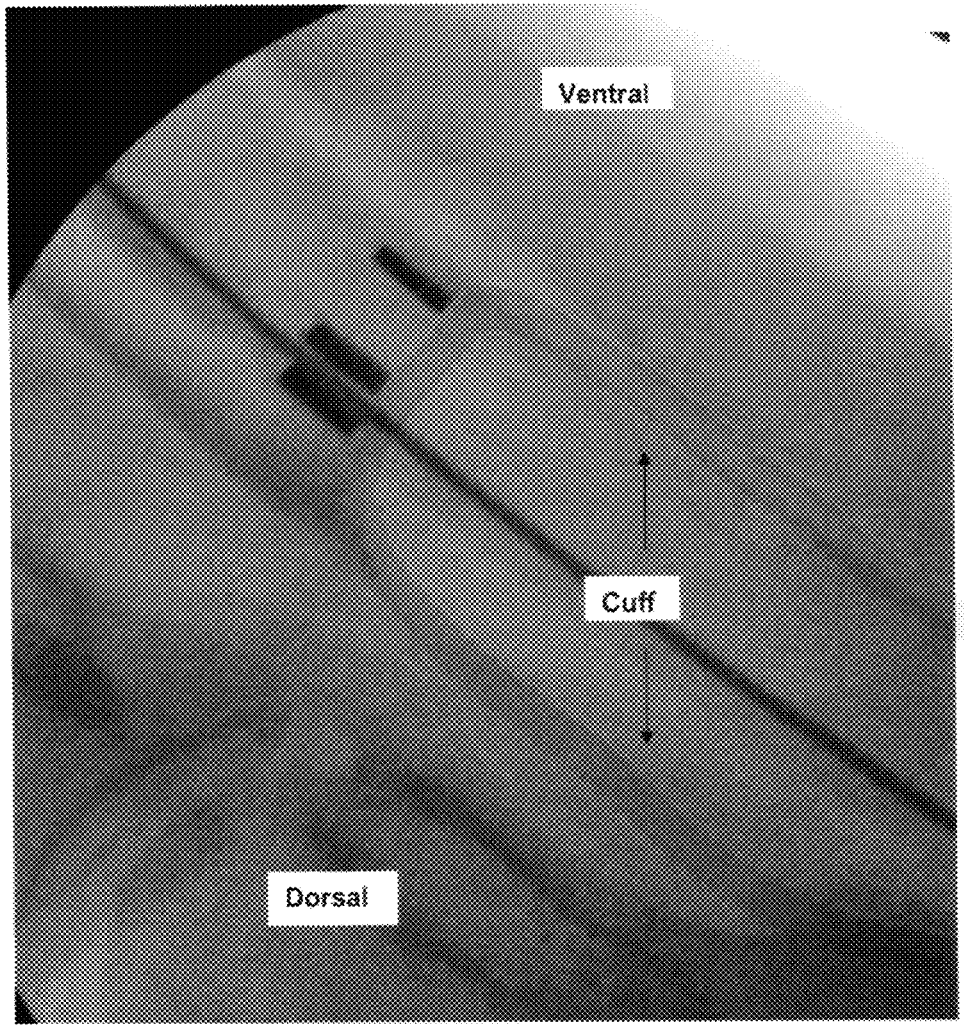

FIG. 13 is a fluoroscopy image of the goat's trachea with the endotracheal tube after the evacuation of the secretions using the prototype device of the present embodiments.

Figure 14:
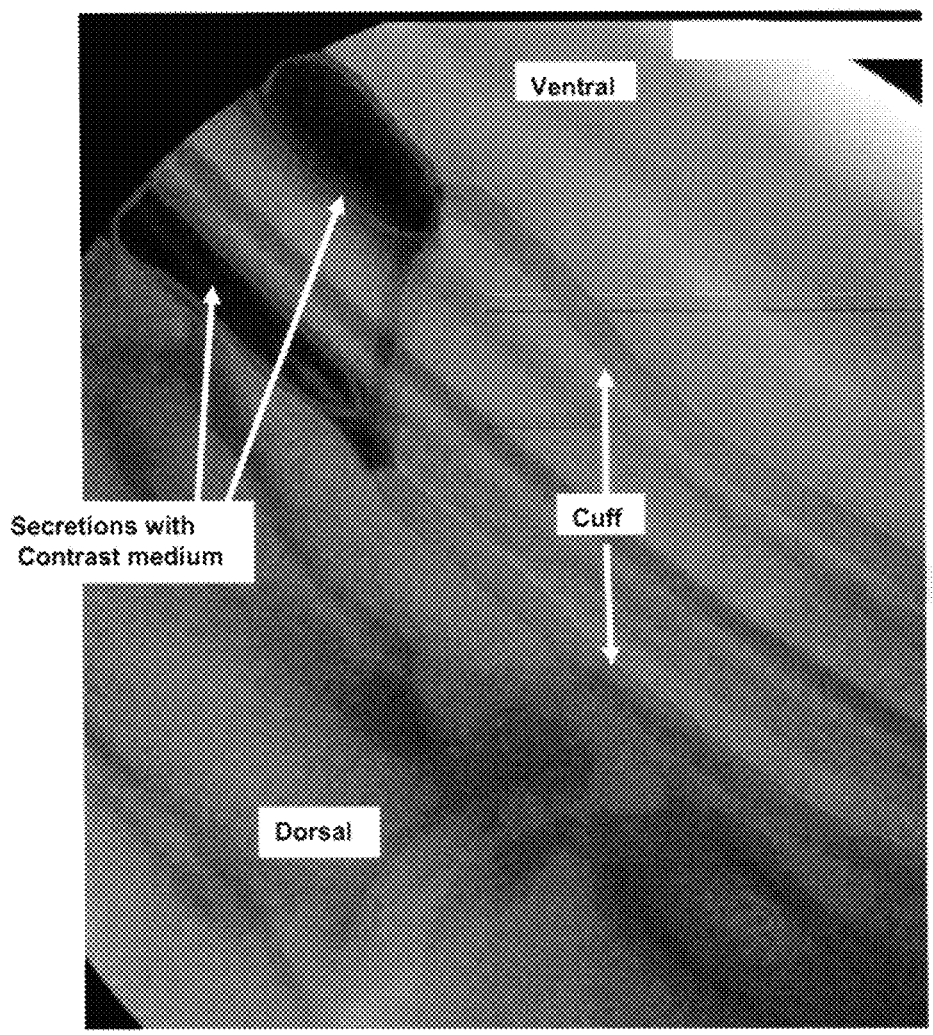

FIG. 14 is a fluoroscopy image of the goat's trachea with a conventional tube before a evacuation of the secretions.

Figure 15:
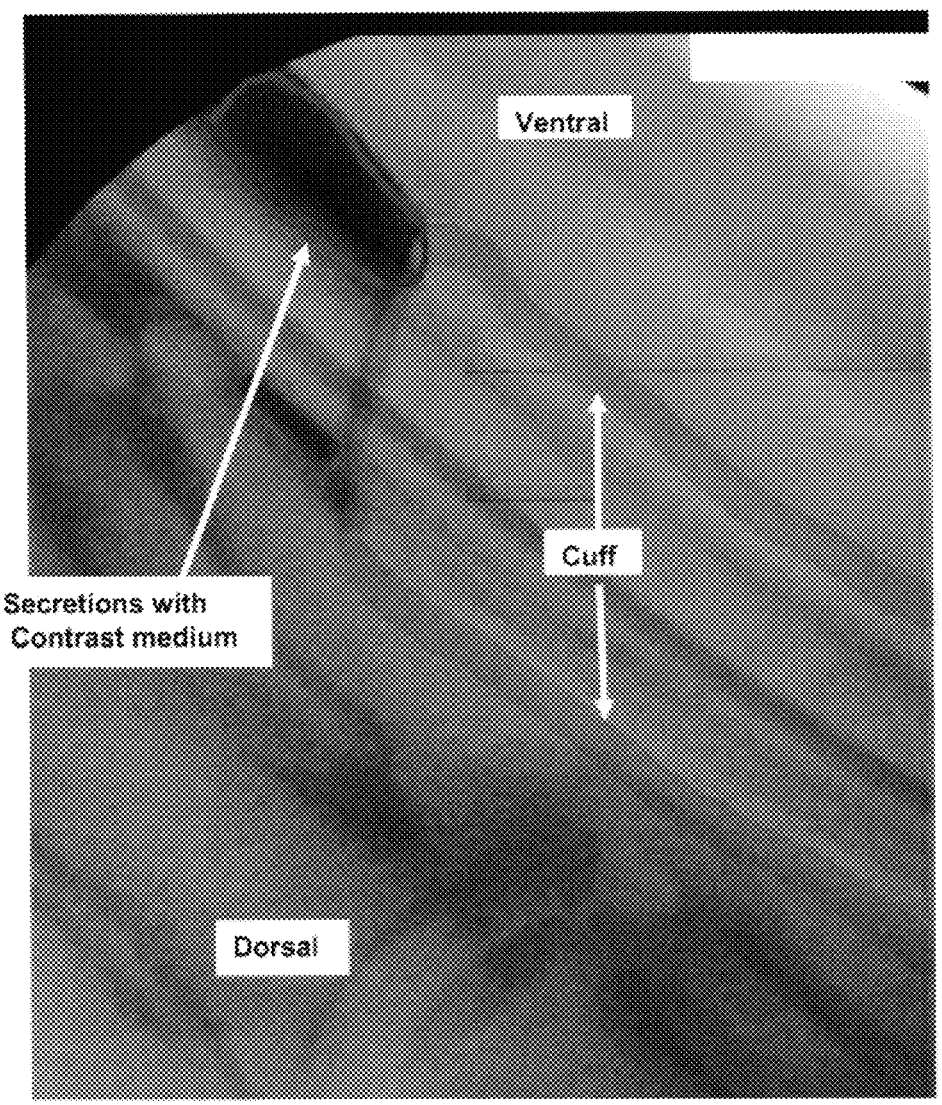

FIG. 15 is a fluoroscopy image of the goat's trachea with the conventional tube after the evacuation of the secretions by rinsing followed by suction.

FIGS. 16A-E are schematic cross-sectional illustrations of a device in embodiments of the invention in which the device includes two piston pumps embodied as syringes arranged such that the withdrawing direction of one syringe is the same as the withdrawing direction of the other syringe.

FIGS. 17A-E are schematic illustrations showing perspective views of the device illustrated in FIGS. 16A-E.

Figure 18A:
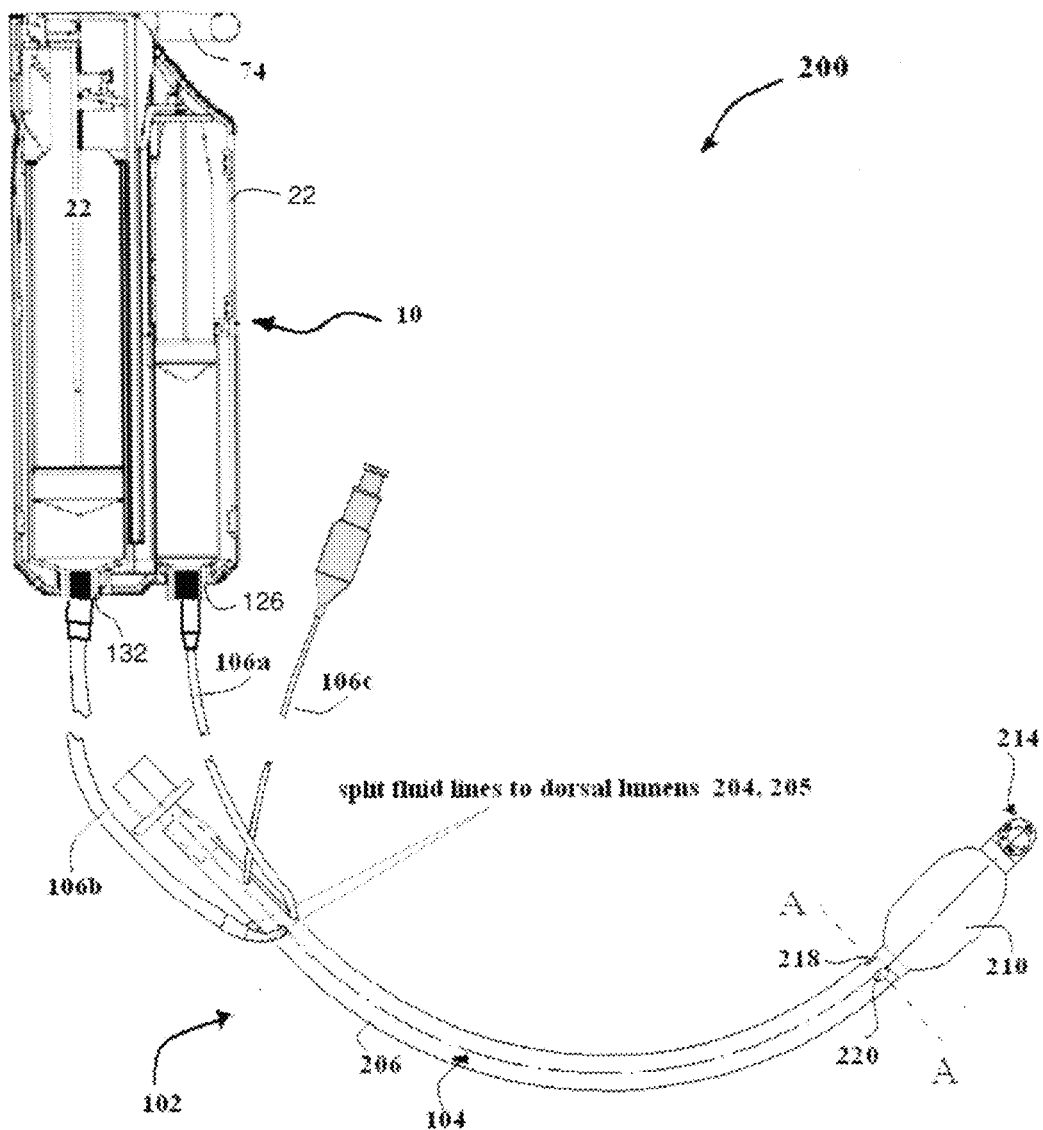
Figure 18B:
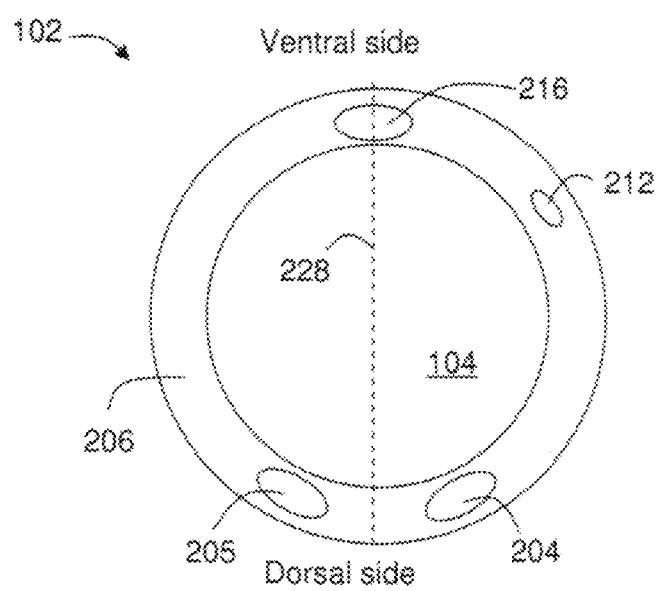

FIGS. 18A-B are schematic illustrations of a kit, according to some embodiments of the present invention.

DESCRIPTION OF SPECIFIC EMBODIMENTS OF THE INVENTION

The present invention, in some embodiments thereof, relates to a hand-held, and optionally a manually-operated, device for irrigating-evacuating a body cavity and specifically, but not exclusively, to a manually operated pump mechanism which can be used to remove secretions from a subglottic region of an intubated subject.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present inventors have previously described endotracheal tubes which are designed for facilitating removal of secretions from a subglottic region using automated pump mechanisms (see WO2007/066332 which is incorporated herein by reference). Although such endotracheal tube configurations are highly effective in reducing complications associated with migration of secretions into the lungs, the requirement for sophisticated pump mechanisms for operability can be limiting In efforts of overcoming these requirements, the present inventors devised a manually-operated pump mechanism which is characterized by at least one of:

(i) a simple design—reduces costs of manufacturing and use;

(ii) simple and easy operation—simple to setup and operate, designed to provide operability familiar to medical personnel;

(iii) single use—reduces risk of contaminations and traverses need for sterilization;

(iv) provides a clear indication of irrigation and of secretions/debris evacuated from an irrigated body cavity; and (v) reducing time and providing more frequent diagnosis by sending the device with evacuated secretions to laboratory for secretions analysis before disposing it.

Thus, according an aspect of some embodiments of the present invention there is provided a device for irrigating and evacuating a body cavity.

As used herein, the term "irrigating" refers to running fluid into and out of the body cavity for the purpose of evacuating secretions, debris and the like.

As used herein, "a body cavity" refers to naturally occurring or artificially formed cavities within tissue structures. One example of a cavity is the space formed below the glottis and above an inflatable cuff of an endotracheal tube or a tracheostomy tube. Other examples including, without limitation, the ear canal, and the intestines.

In embodiments of the invention in which the device is adapted for manually irrigating and evacuating the space defined between the tracheal wall and an endotracheal tube or a tracheostomy tube below the glottis and above the inflatable cuff, the device is termed Manual Aspiration of Subglottic Secretions (MASS) device.

The device of the present embodiments includes a manually-operated pump mechanism capable of delivering a volume of fluid to the body cavity while concomitantly withdrawing a volume of fluid from the body cavity (through suction). Such delivery is typically effected through two fluid lines (delivery and suction) each separately connected to the pump mechanism of the present embodiments at one end, while the opposite end of each fluid line is disposed within the body cavity or connected to a device being in fluid communication with the body cavity (e.g. an endotracheal tube such as that shown in FIGS. 2A-E or FIGS. 4A-E or 5A-D or that described in WO2007/066332, or a tracheostomy tube such as that shown in FIGS. 2F-J or FIG. 4F-4J or 5E-5H).

Manually operated pump mechanisms such as syringes are relatively inexpensive to fabricate and easy to operate. However, such mechanisms are typically limited in that each stage of an irrigation procedure (pumping fluid in and pumping fluid out) requires a separate manual operation of the pump piston (syringe plunger). Although mechanical pumps capable of continuous operation (e.g. peristaltic) can be manually operated to circulate a fluid through a cavity they can be difficult to operate and are less suitable for use in medical applications which require periodic rapid irrigation with low volumes of fluid under sterile conditions.

The manually operated pump mechanism of the present embodiments is configured for delivering a volume of fluid into the cavity while simultaneously or sequentially (or semi-sequentially) withdrawing that volume in a single stage of operation thus enabling rapid and easy irrigation of the body cavity and traversing the limitations of prior art devices such as simple syringes.

During the operation phase in which the pump mechanism delivers fluid to the body cavity and simultaneously withdraw fluid from the body cavity, there is always a linear relation between the volumetric flow rate $Q_1$ at which the fluid is delivered and the volumetric flow rate $Q_2$ at which fluid is withdrawn. For example, $Q_2=Q_1$, or $Q_2=aQ_1$ or $Q_2=aQ_1+b$, where a and b are constants. In some embodiments of the present invention b=0.

The manually operated pump mechanism of the present embodiments is optionally and preferably also configured to enable a priming operation in which a first volume of fluid is first delivered into the cavity without simultaneous withdrawal of that fluid. Such a priming stage fills the suction line and optionally partially fills the body cavity so as to establish a fluid continuum between the pump mechanism and the body cavity and prevent compressible gas voids within suction line.

This feature is particularly important since air filled suction lines can collapse due to tissue occlusion of suction ports. Under suction pressure, tissue sucked into a suction port can cause a suction line to collapse. If the suction line is filled with a fluid such as saline (which unlike air is not compressible) a continuum is created between the pump mechanism and the fluid in the body cavity thereby preventing collapse of the suction line and occlusion of the suction line.

To enable such 'priming' of fluid lines and especially the fluid suction line, the mechanism of the present embodiments enables a two stage operation in which in a first stage (priming) a first volume of fluid is delivered to the body cavity via the irrigation mechanism (without simultaneous fluid withdrawal), followed by a second stage of operation (irrigation using a second fluid line that delivers fluid into the cavity) in which delivery and simultaneous withdrawal of a second (and typically larger) volume of fluid is effected. Preferably, the second (delivery) line is also primed with fluid prior to delivery and simultaneous withdrawal.

Several configurations of the device of the present embodiments can be used to enable such functionality, one preferred configuration of the present device includes a pump mechanism constructed from two operably linked piston pumps having opposingly operable pistons actuatable via a single manual operation.

Such linked operation can be used to deliver fluid into the body cavity from a first piston pump while simultaneously withdrawing fluid from the body cavity through the second and operatively linked piston pump.

Several piston pump configurations can be used to provide such operability. One configuration which is particularly useful for medical applications is a dual syringe configuration having operatively linked plungers.

A device configuration using two interconnected syringes is easy and inexpensive to manufacture, can be disposed of with ease following a single use (thereby lending itself to medical applications) and provides the treating physician with familiar operability.

FIGS. 1A-D illustrate one embodiment of a dual syringe device which is referred to herein as device 10.

Device 10 includes two pumps 12, for example, piston pumps, shown in FIGS. 1A-D as syringes. Each syringe is constructed from a barrel (with nozzle 14—shown on one syringe) housing a plunger 18 having a seal (not shown) and back stop 34. Syringes 12 are fabricated using materials and methods well known in the art.

One or both plungers 18 can include a spring element for facilitating plunger withdrawal from the barrel once plunger 18 is pushed in. Sprung plungers enable a greater degree of control over plunger activation and as such can be advantageous in cases where fluid delivery has to be carefully controlled. Spring loaded plunger configurations are well known to the ordinary skilled artisan.

Syringes 12 can be connected using removable or non-removable attachment mechanisms. FIGS. 1A-D illustrate configuration of device 10 in which syringes 12 are attached to a housing 22. Housing 22 can be fabricated to accommodate syringes of variable sizes, volumes and plunger stroke lengths. The configuration shown in FIGS. 1A-D includes syringes 12 of non identical volumes (asymmetric configuration), although symmetric configurations in which syringes 26 and 32 are identical can be used in device 10. In asymmetric configurations, a syringe 12 used for suction (32) can be configured to generate a suction volume per plunger 18 stroke (see the configuration of FIGS. 3A-C which is further described hereinunder) which is greater than the delivery volume of syringe 26. This enables suctioning of the irrigation fluid delivered from syringe 26 as well as any fluid contained in the cavity (e.g. secretions etc).

The volume of each syringe, as well as plunger 18 stroke length are selected according to the irrigation procedure, for example, in the case of subglottic irrigation, each syringe can contain about 2-10 ml deliverable through a plunger stroke length of about 5-10 cm. Other amounts are not excluded from the scope of the present invention. FIGS. 1A-D illustrate syringes 12 in an 'over and under' configuration however, other arrangements such as that of the configuration shown in FIGS. 2A-8B are also envisaged.

Figure 1A:
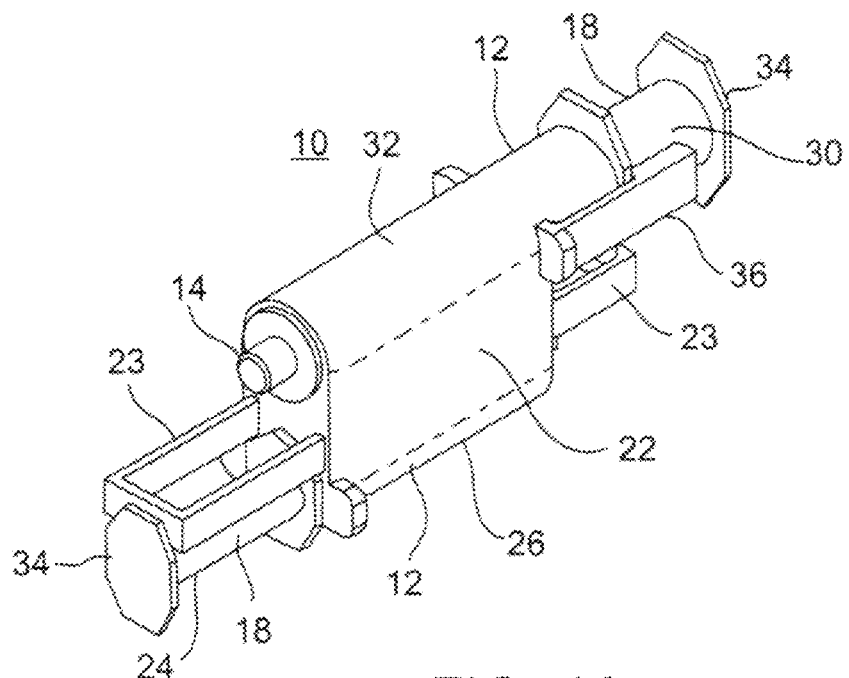
Figure 1B:
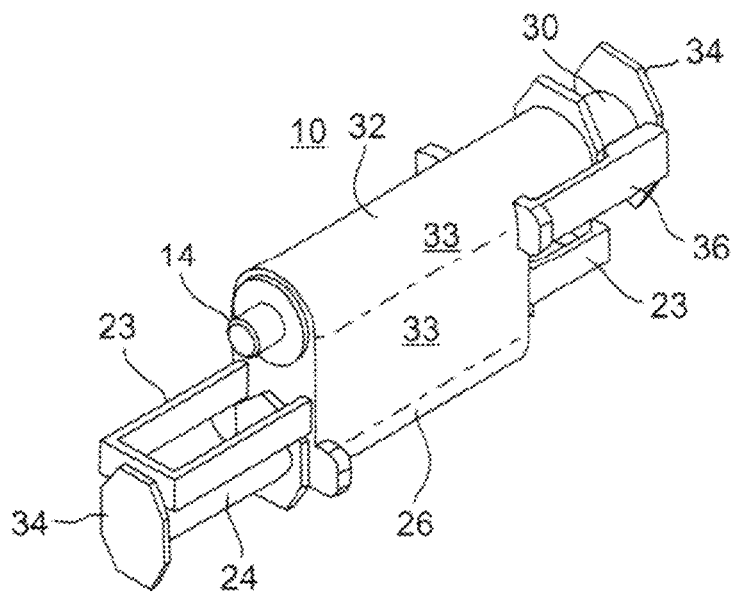
Figure 1C:
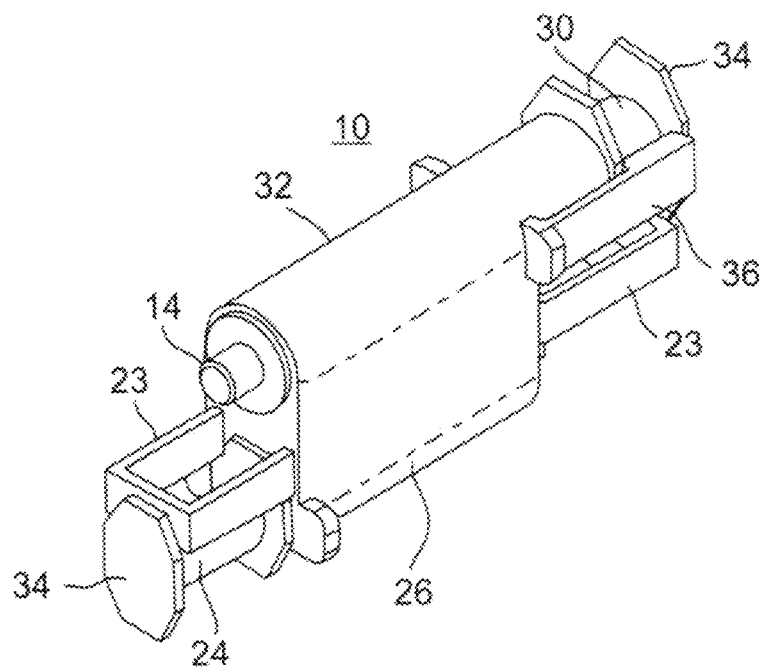
Figure 1D:
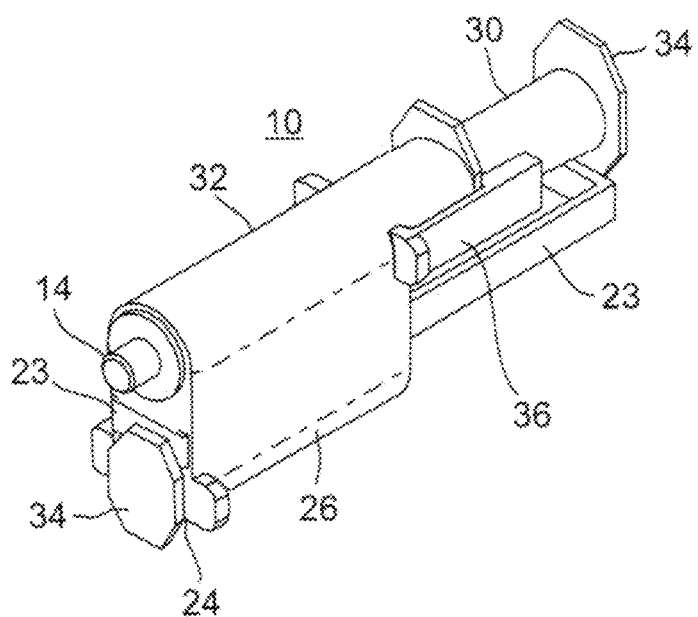

As is mentioned hereinabove, device 10 of the present embodiments is configured so as to provide fluid delivery and withdrawal via a single manual operation. To enable such functionality, plungers 18 of syringes 12 are operatively linked via element 23 to move in opposite directions (with respect to the syringe barrels). Thus, when plunger 24 of syringe 26 is pushed into barrel 28 effectively delivering any fluid contained therein (through nozzle 14—not shown), element 23 draws plunger 30 of syringe 32 out of barrel 32 creating a suction force capable of withdrawing fluid through nozzle 14 (FIGS. 1C-D). Element 23 shown in FIGS. 1A-D is an elongated frame disposed between end stops 34 of syringes 12 and set within grooves in housing 22 (enabling element 23 to slide back and forth). Element 23 can be interchangeable to provide varying functionality.

Operatively connecting plungers 18 via element 23 enables single stage irrigation, however, it negates any independent movement of plungers 18 and thus prevents syringe 26 or 32 from being used to prime a suction line.

Several approaches can be used to enable such functionality. For example, syringe 24 and/or 30 can be removed from housing 22 and used for priming a suction line and/or rinsing lines prior to evacuation, or element 23 can be configured to enable some non-linked movement of plungers 18 through a preset movement range beyond which movement of plungers 18 is linked.

The latter configuration is shown in FIGS. 1A-D, 2A-J and 3A-C. As is seen in FIG. 1A, plunger 30 of syringe 32 is free to move a preset distance without backstop 34 contacting element 23. Such free movement of plunger 30 enables use of syringe 32 for delivering a preset volume of fluid through nozzle 14 without activating movement of plunger 24; this enables the priming of a suction line described above. Once plunger 30 is depressed such that backstop 34 engages limiter 36 and delivery of fluid from syringe 32 is complete (FIG. 1B), operating plunger 24 of syringe 26 slides element 23 in the direction of backstop 34 of syringe 32 until element 23 contacts backstop 34 of syringe 30 (FIG. 1C), this phase can also include non-linked movement in order to deliver a predetermined amount of fluid for priming the fluid delivery line (with excess fluid delivered into the body cavity). In any case, once element 23 contacts backstop 34 of syringe 32 inward movement of plunger 24 forces plunger 30 out of syringe 32 (FIG. 1D) thereby generating simultaneous fluid delivery from syringe 26 and suction in syringe 32.

Thus, a single operation of pushing in plunger 24 can be used to optionally prime a fluid delivery line and thereafter simultaneously deliver and suction fluid through two separate delivery nozzles.

In the configuration shown in FIGS. 1A-D, element 23 is designed to provide each plunger 18 with some independent movement, it will be appreciated however, that an element 23 which does not enable independent movement of plungers 18 or one that enables more independent movement can also be used.

Although the configurations shown in FIGS. 1A-8B include two opposingly mounted syringes (whether end to end or over and under), wherein the withdrawing direction of one syringe is parallel to the ejecting direction of the other syringe, this need not necessarily be the case since, in some embodiments the syringes are mounted in the same direction (i.e. nozzles on the same side of device 10), wherein the withdrawing direction of one syringe is opposite to the ejecting direction of the other syringe. Such configurations can employ an element 23 configured to translate movement of one plunger to opposite movement of another plunger. For example, element 23 can be a beam attached at ends thereof to plungers 18 and to a hinged element in the middle thereby functioning as a seesaw between the two plungers, or cogwheel that connects two opposite elements. A representative and non-limiting example of this embodiment is described hereinafter with reference to FIGS. 16A-E and 17 A-E.

Device 10 of the present embodiments can be used for irrigating body cavities such as tissue voids filled with pus, by clearing the pus while preventing shrinkage of surrounding tissue by filling the void created with antiseptic or other therapeutic fluid. The present device can also be used to clear obstructions in vessels such as urinary. Opposite sides of the vessel can be connected to delivery and fluid lines and simultaneously rinsed and suctioned with saline or a therapeutic fluid to clear and suction out an obstruction.

Automatic irrigation systems and pumps are limited in that they may cause a collapse of a cavity due to large and rapid suction pressures. By providing manual control over irrigation and suction, the present embodiments enable an operator to carefully control irrigation and suction and thus clear cavities of accumulated fluids and debris without compromising the integrity of the cavity or damaging tissue surrounding and defining such cavity.

One preferred use for the present device is irrigation of a subglottic region in intubated patients, either during oral endotracheal intubation or during tracheostomy intubation. In such cases, the present device preferably forms a part of a system which also includes an endotracheal or tracheostomy tube having at least two separate fluid lines. One example of a suitable endotracheal tube is described in WO2007/066332 which is incorporated herein by reference.

FIGS. 2A-J illustrate an intubation system 50 which comprises device 10 connected to a tube 60 through fluid delivery line 52 and a suction line 54. Tube 60 can be an endotracheal tube, as schematically illustrated in FIGS. 2A-E or a tracheostomy tube as schematically illustrated in FIGS. 2F-J. Tube 60 includes cuff 62, fluid suction port 66 and fluid delivery port 68. Ports 66 and 68 are in fluid communication with external suction tube 54 and external delivery tube 52 respectively.

Device 10 of FIGS. 2A-J comprises syringes 12 which are connected back to back with plungers 18 interconnected via element 23.

Element 23 in this case is a strut which is compressible to a folded configuration of a predetermined length or stretched to a linear configuration of a predetermined length. This length change in element 23 provides each plunger 18 with a preset range of independent movement.

Figure 2B:
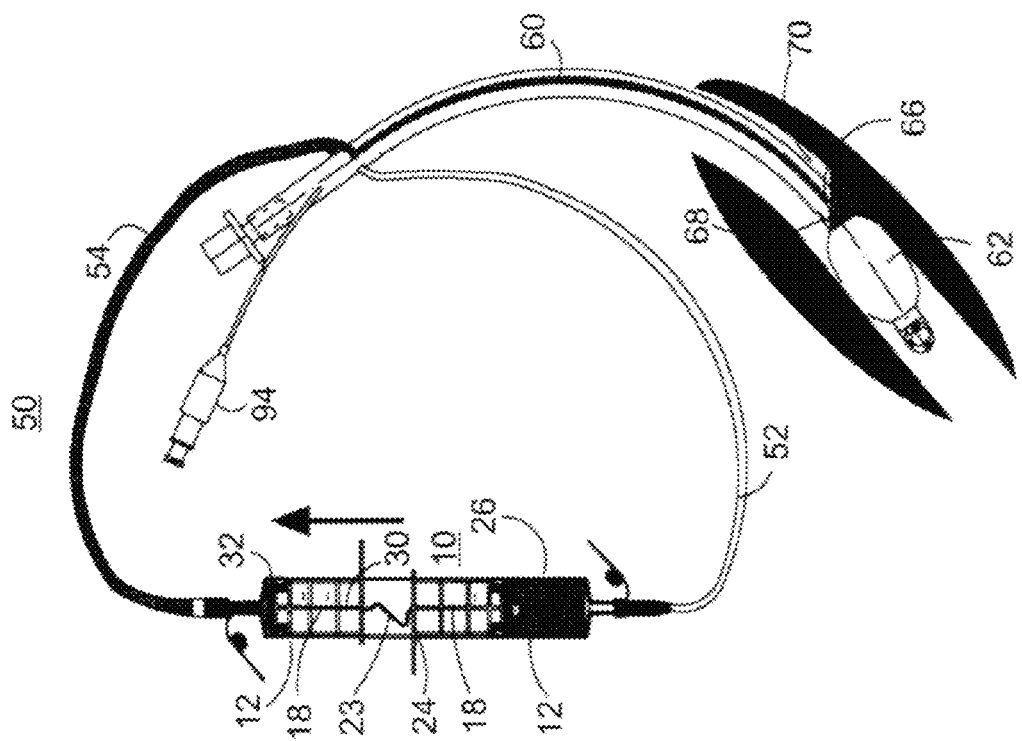
Figure 2A:
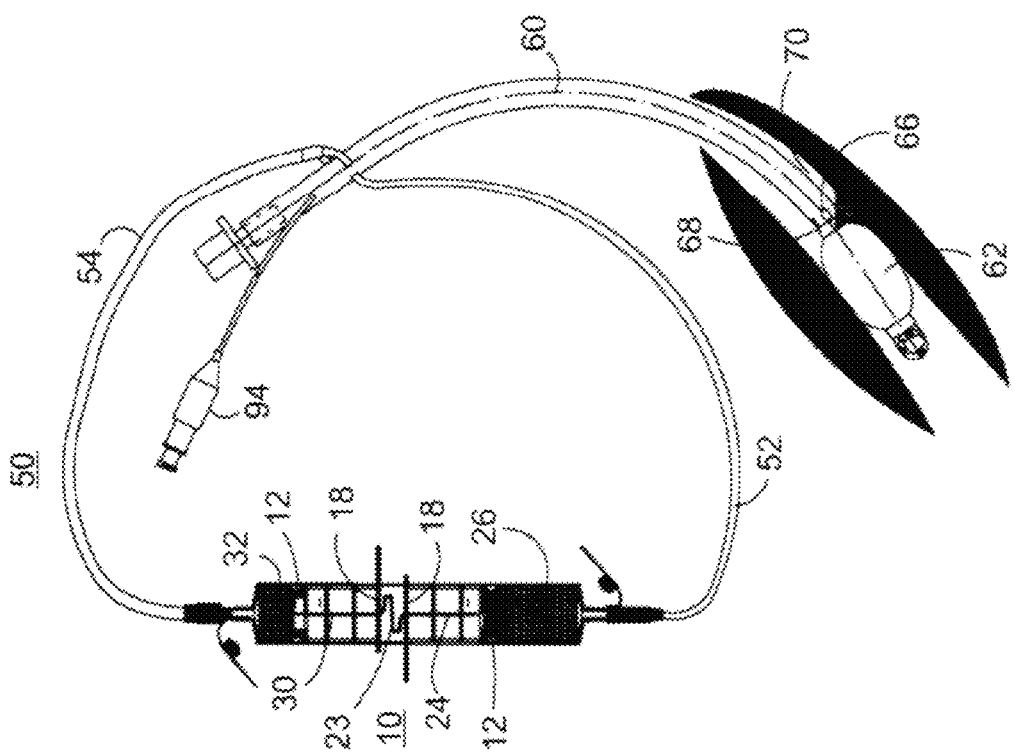
Figure 2C:
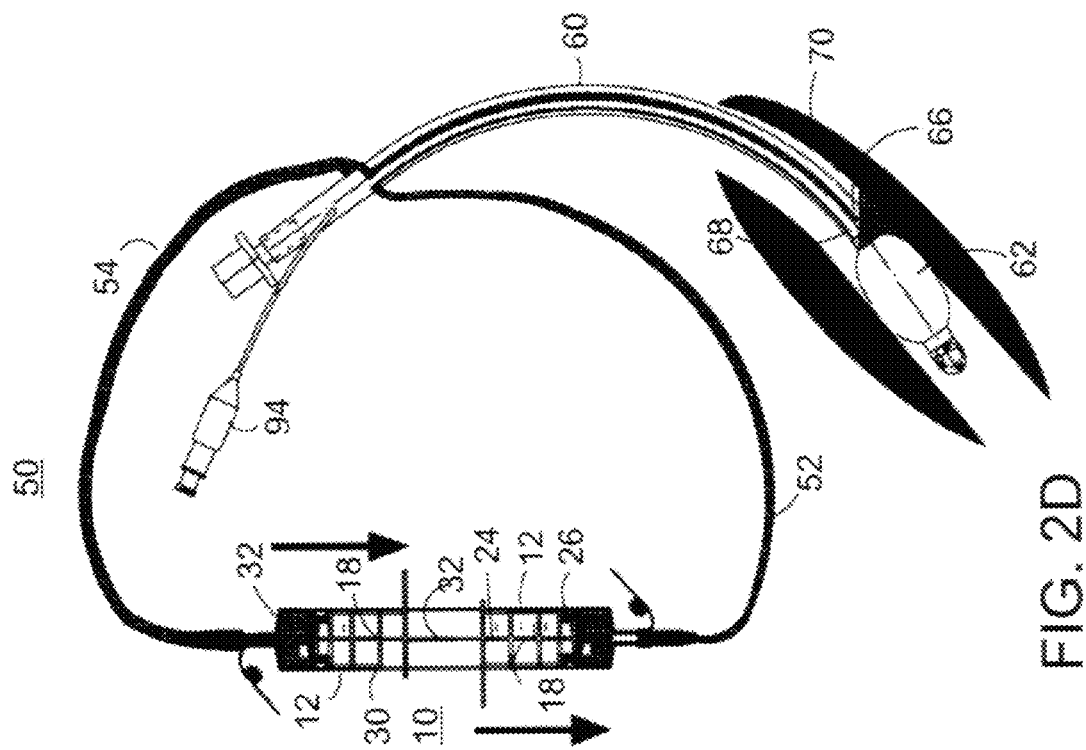
Figure 2D:
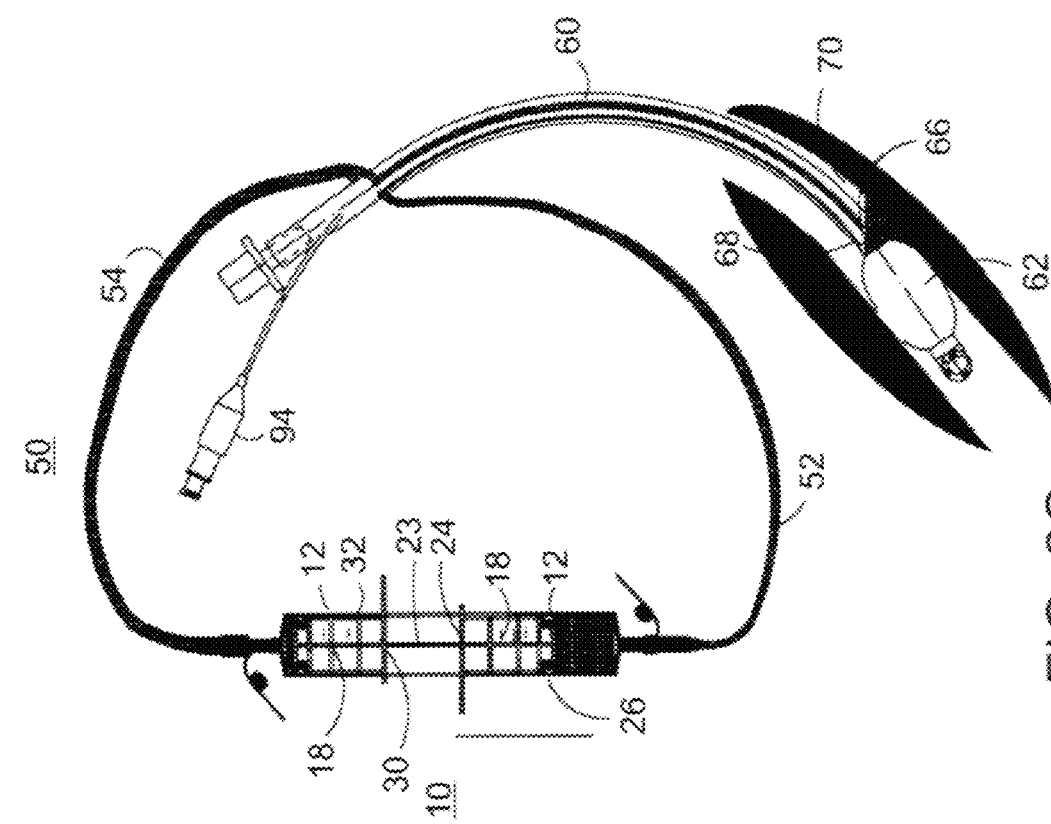
Figure 2F:
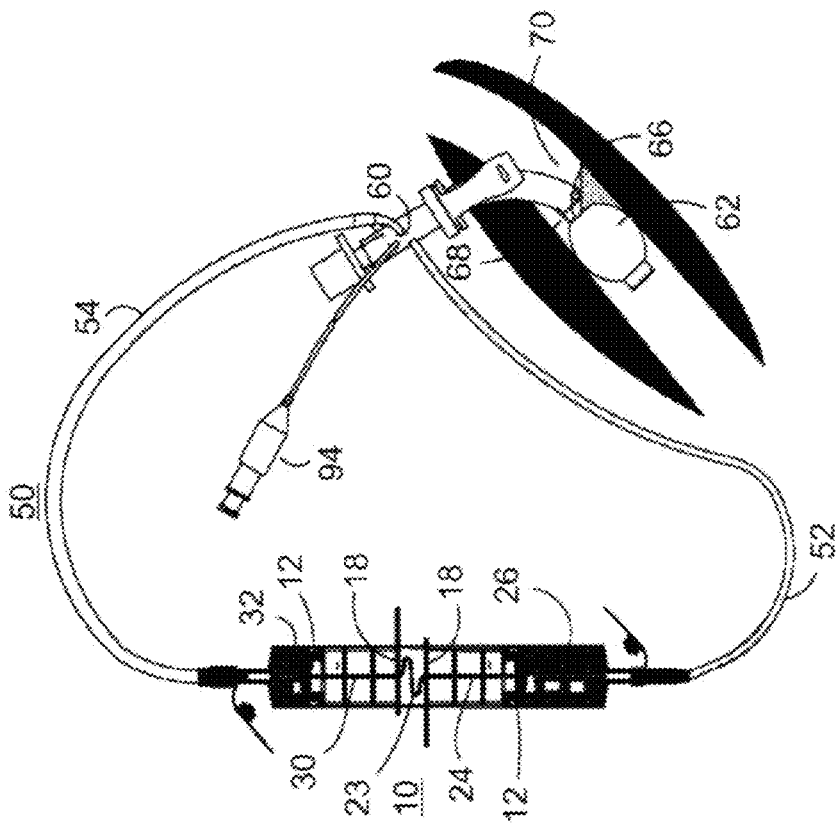

FIGS. 2A and 2F illustrate system 50 in the initial state. Syringe 32 is filled with about 4 ml of a rinsing solution (saline or/and diluting fluid or/and antiseptic fluid), while syringe 26 is filled with about 12 ml of the same solution. Other amounts are not excluded from the scope of the present invention. Element 23 is shown in the compressed state thus allowing independent movement of plungers 24 and 30.

Figure 2E:
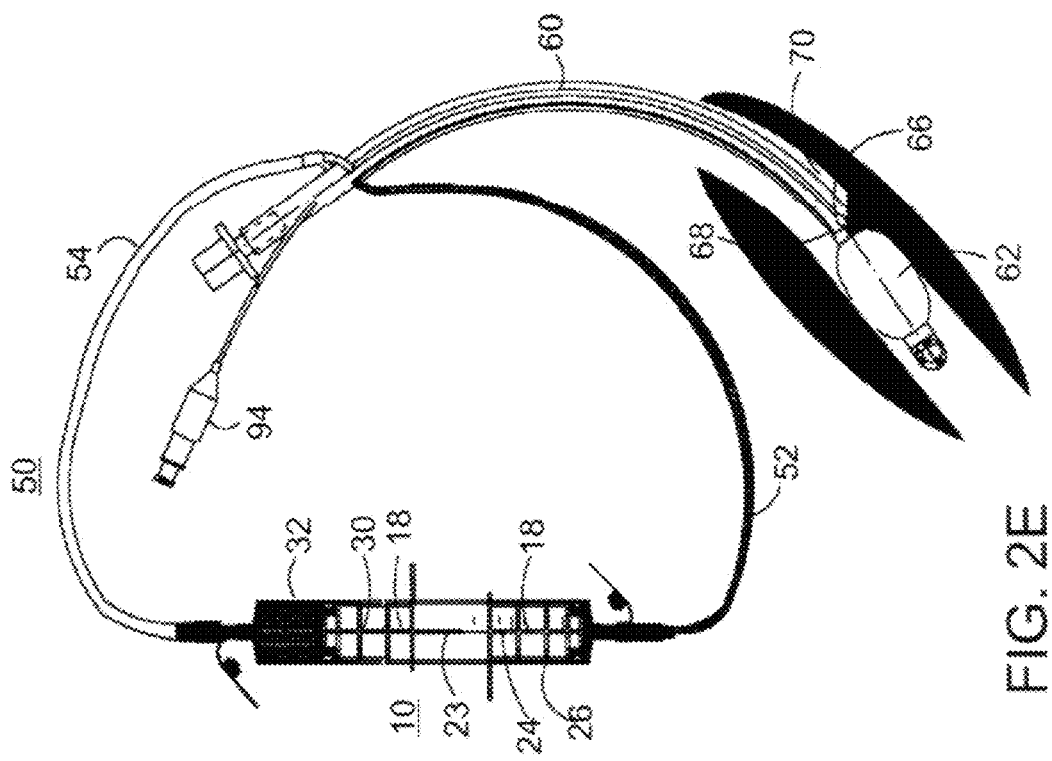
Figure 2H:
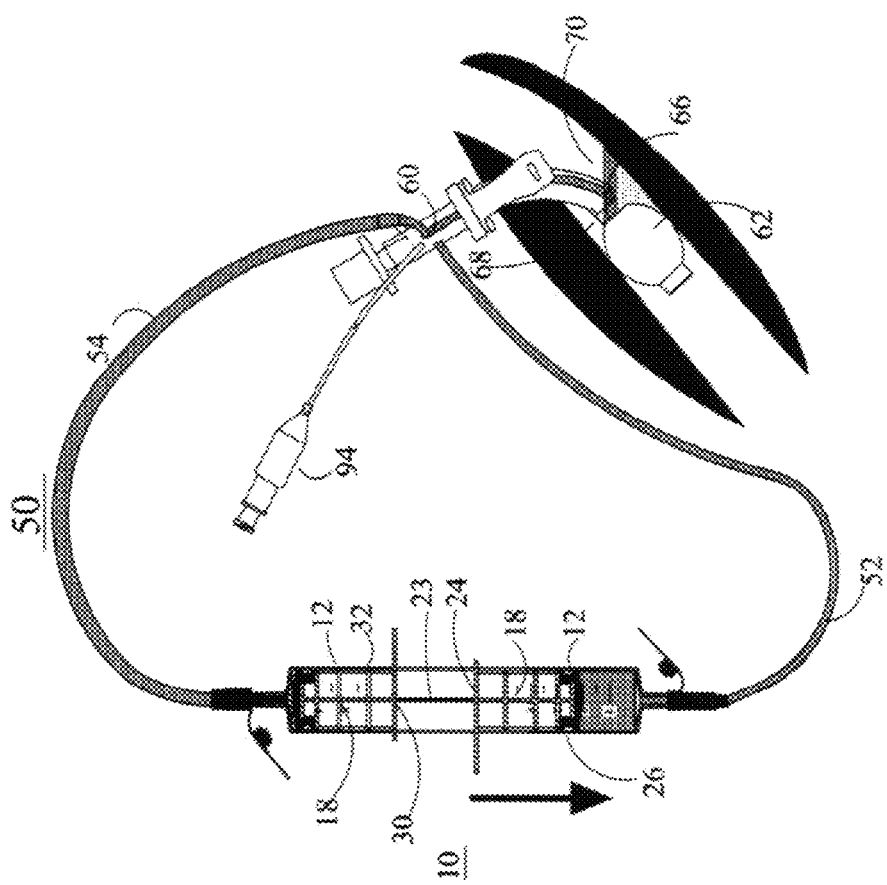
Figure 2G:
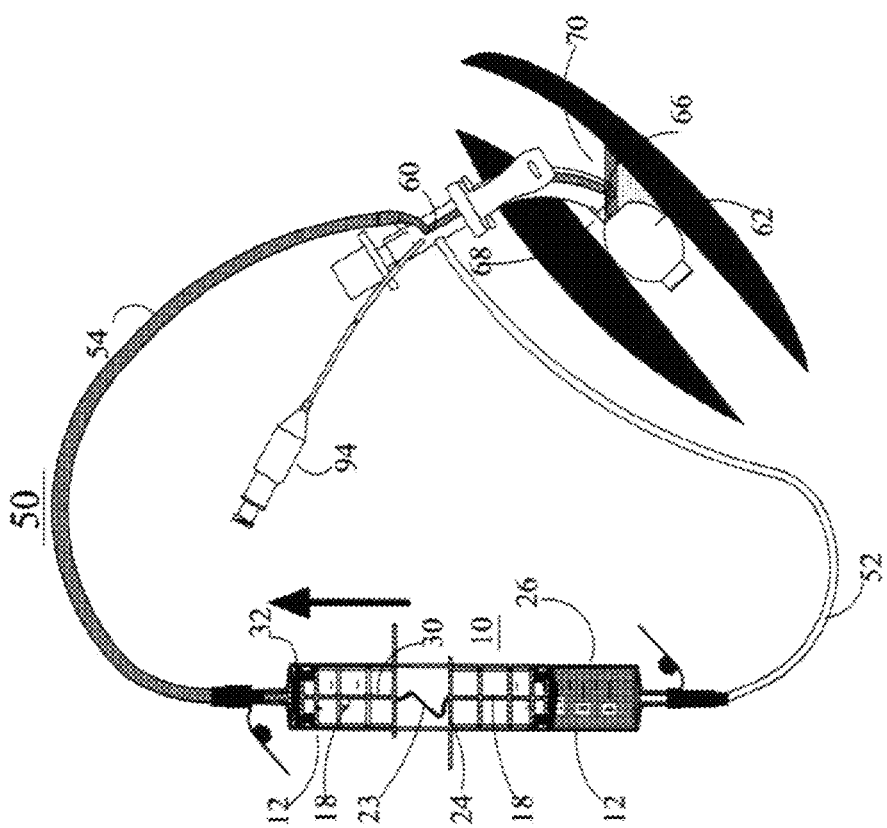
Figure 2J:
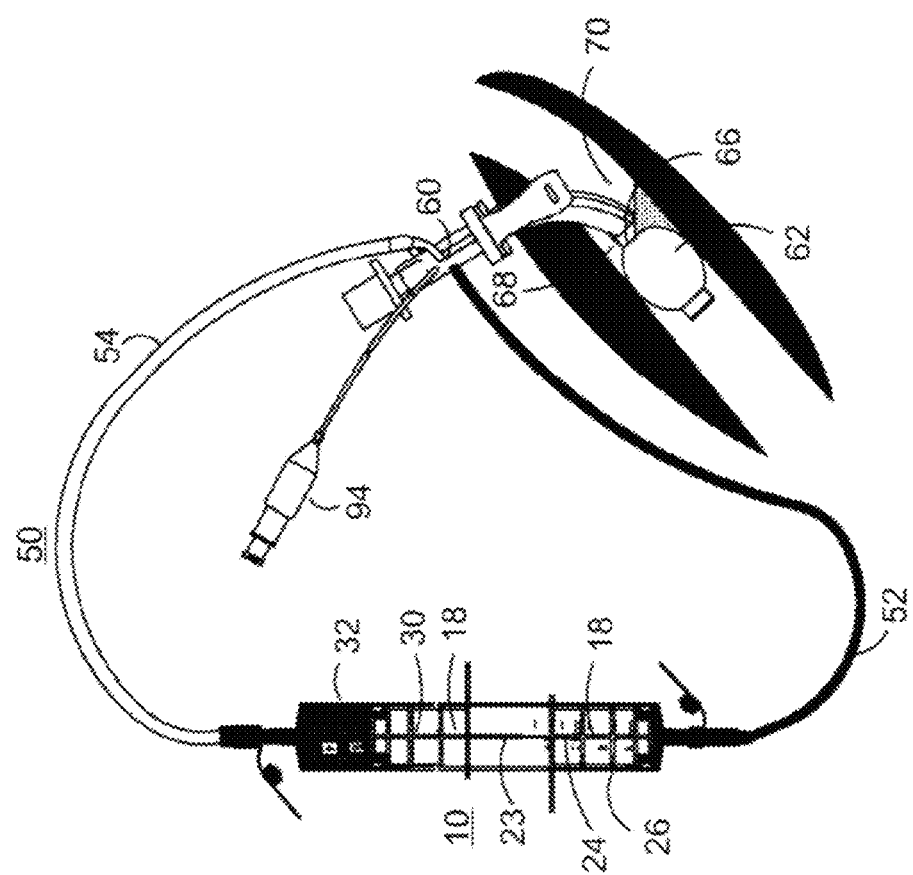
Figure 2I:
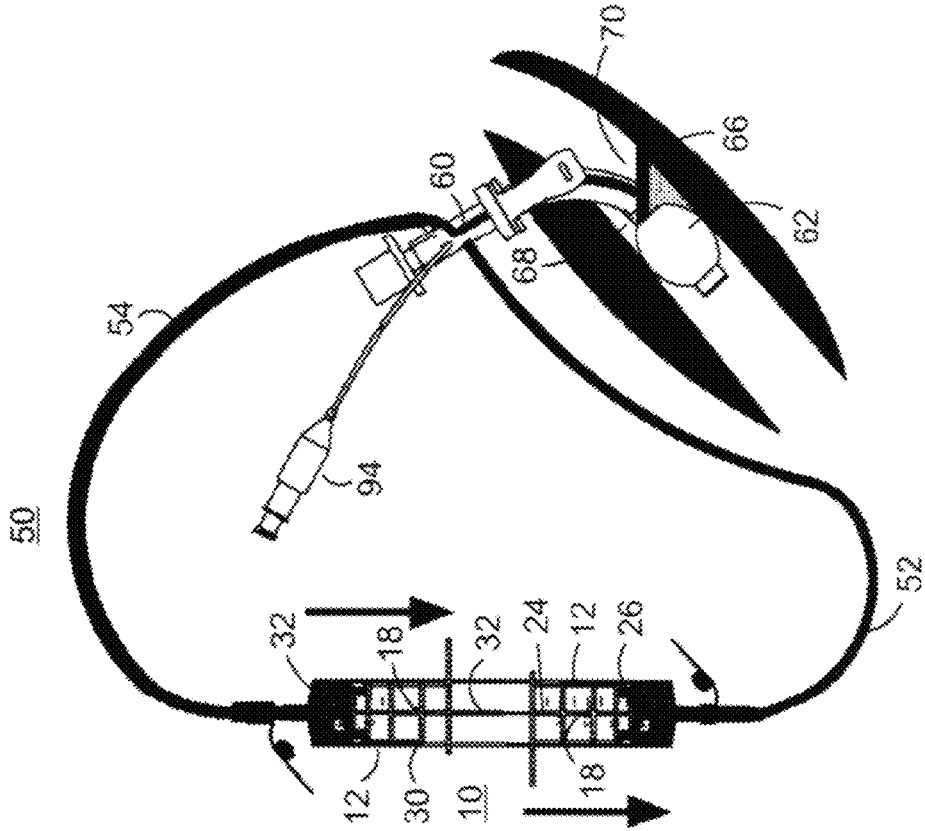

FIGS. 2B-C and 2G-H illustrate priming of suction line 54 via actuation of plunger 30 (arrow FIGS. 2B and 2G); excess rinsing solution fills subglottic region 70. FIGS. 2C and 2H illustrate priming of rinsing line 52 via actuation of plunger 24; excess rinsing fills subglottic region 70. Once plungers 24 and 30 are fully actuated in, element 23 straightens (FIGS. 2C and 2H). Now plunger 24 is actuated (arrow FIGS. 2C and 2H) to deliver rinsing solution from syringe 26 and at the same time draw out plunger 30 (FIGS. 2D and 2I) creating suction in syringe 32. Concomitant delivery and suction irrigates subglottic region 70 and removes any secretions accumulated in this cavity into syringe 32 (FIGS. 2E and 2J). Device 10 can then be disconnected from lines 52 and 54 which are then capped. Device 10 can then be disposed of or sent to laboratory for diagnosis purposes and replaced with a new device 10 if additional irrigation/evacuation is needed.

Device 10 depicted in FIGS. 2A-J employs a symmetric syringe configuration which, at the concomitant delivery-suction phase, suctions a volume of fluid which is identical to that delivered.

The configuration shown in FIGS. 3A-C employs syringes 12 of different barrel and plunger diameters—syringe 32 has a larger barrel diameter (and hence larger volume per stroke length of plunger 18) than that of syringe 26.

Such an asymmetric syringe configuration enables syringe 32 of device 10 to suction a larger volume of fluid than that delivered by syringe 26 of device 10 during the concomitant delivery-suction phase (FIG. 3C). This enables device 10 to more effectively clear fluids from a cavity, especially one which includes excess volume of natural secretions (e.g. subglottic cavity).

Device 10 of FIGS. 3A-C incorporates an element 23 configuration which enables independent movement of syringe 32 through a locked tongue and groove configuration. This configuration of element 23 enables limited movement of tongue 25 in groove 27. As is shown in FIGS. 3A-C, once syringe 32 is completely pushed in, tongue 25 moves out of groove 27 to a locked position (FIG. 3B), pushing in plunger 24 of syringe 26 draws out plunger 30 of syringe 32 generating a suction force in syringe 32. It will be appreciated that in this configuration plunger 30 can be modified to include a spring such that the step of priming, in which plunger 30 is pushed in, loads the spring (e.g. compresses it) and locks element 23 with the spring loaded. Releasing element 23 releases the spring and automatically withdraws plunger 30 thereby automatically pushing in plunger 24.

FIGS. 4A-J illustrate the stages of operation of embodiments of the present device, in which the device comprises a spring that is stretched when a lock is release. FIGS. 4A-E illustrate a system in which the device is connected to an endotracheal tube and FIGS. 4F-J illustrate a system in which the device is connected to an tracheostomy tube. The spring facilitates automatic of the suction lines, wherein the operator pushes the lever only in one direction to the end. The spring can be unidirectional or bidirectional. In the illustrations of FIGS. 4A-J a unidirectional spring is employed.

Figure 4A:
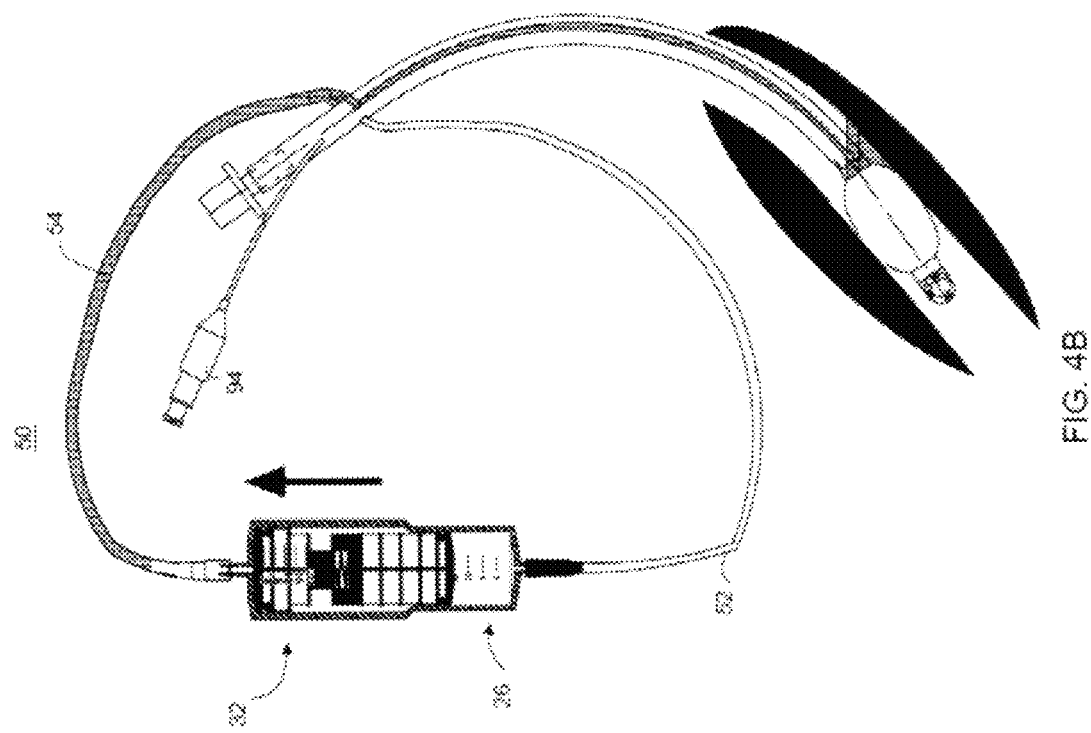
Figure 4B:
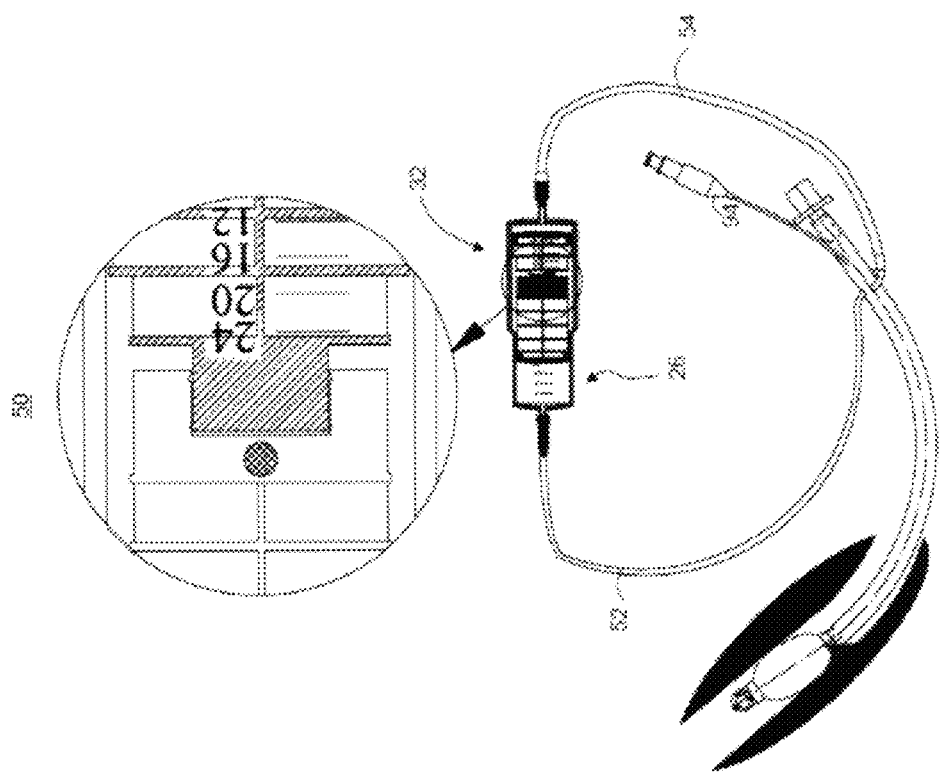
Figure 4D:
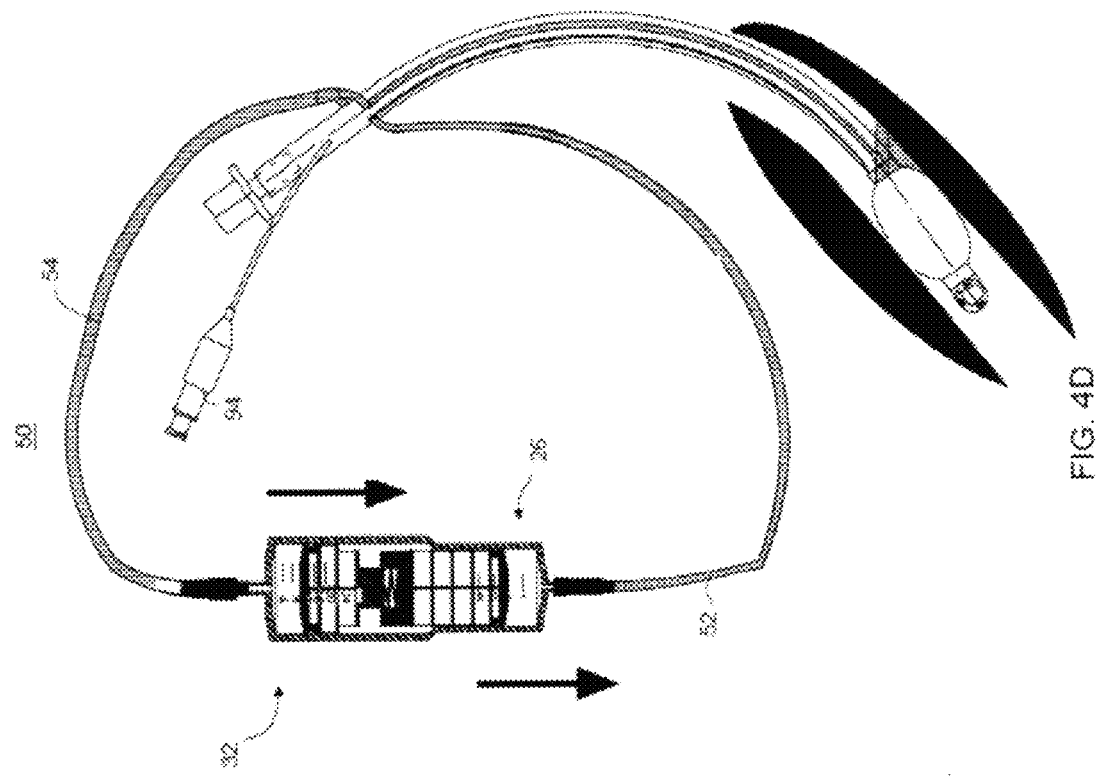
Figure 4C:
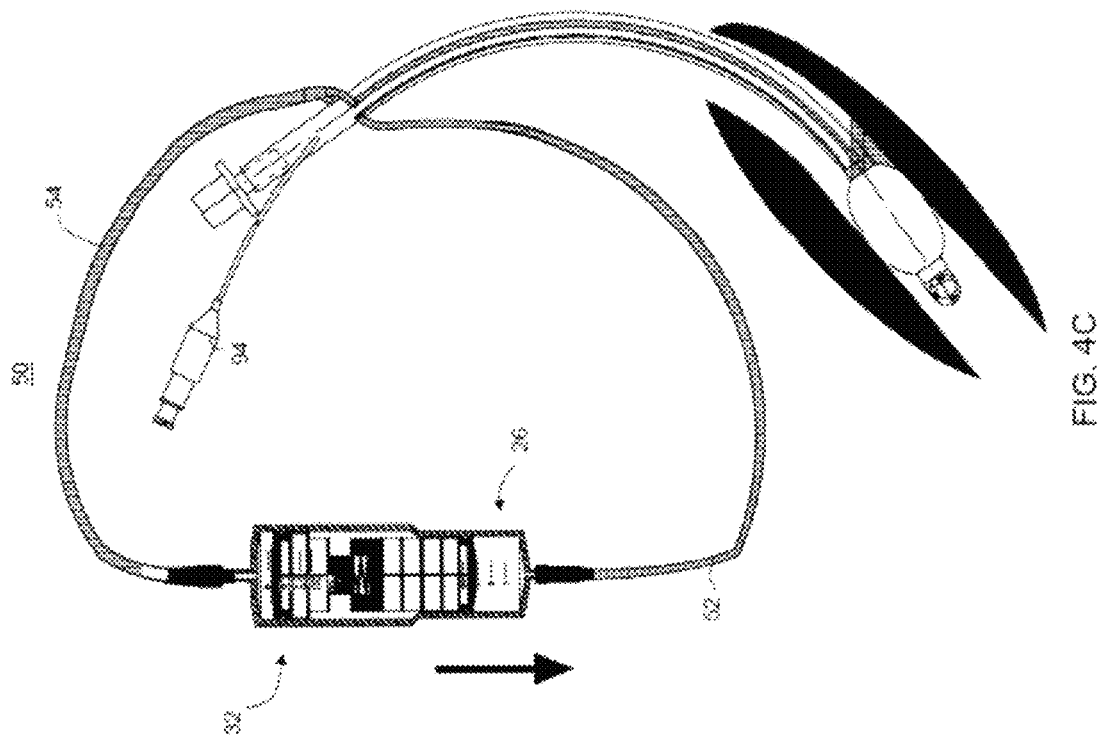
Figure 4F:
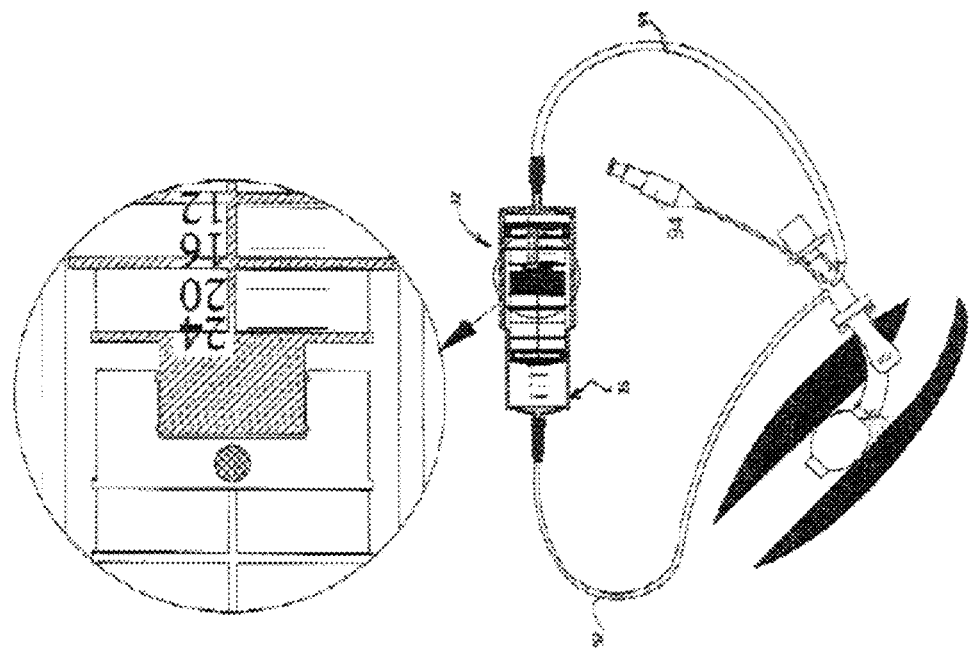
Figure 4E:
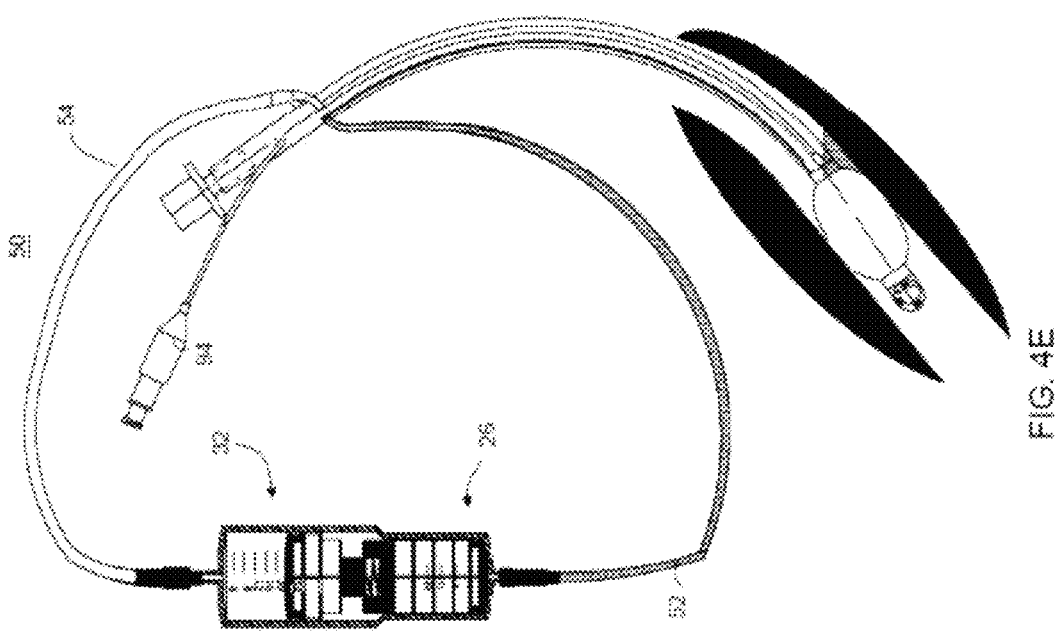

FIGS. 4A and 4F illustrate system 50 in the initial state. The syringe is filled with, e.g., 4 ml of rinsing solution while the other syringe is filled with, e.g., 12 ml of the same solution, as further detailed hereinabove. Other amounts are not excluded from the scope of the present invention. FIGS. 4B-C and 4G-H illustrate priming of the suction line (FIGS. 4B and 4G), and rinsing line (FIGS. 4C and 4H), as further detailed hereinabove. FIGS. 4D and 4I illustrate the simultaneous rinsing (via the rinsing line) and suction (via the suction line). Concomitant delivery and suction irrigates the subglottic region and removes any secretions accumulated in this cavity (FIGS. 4E and 4J).

FIGS. 5A-H illustrate the stages of operation of the device in embodiments in which the device comprises a bidirectional spring that is stretched when a lock is release. FIGS. 5A-D illustrate a system in which the device is connected to an endotracheal tube and FIGS. 5E-H illustrate a system in which the device is connected to an tracheostomy tube.

Figure 5B:
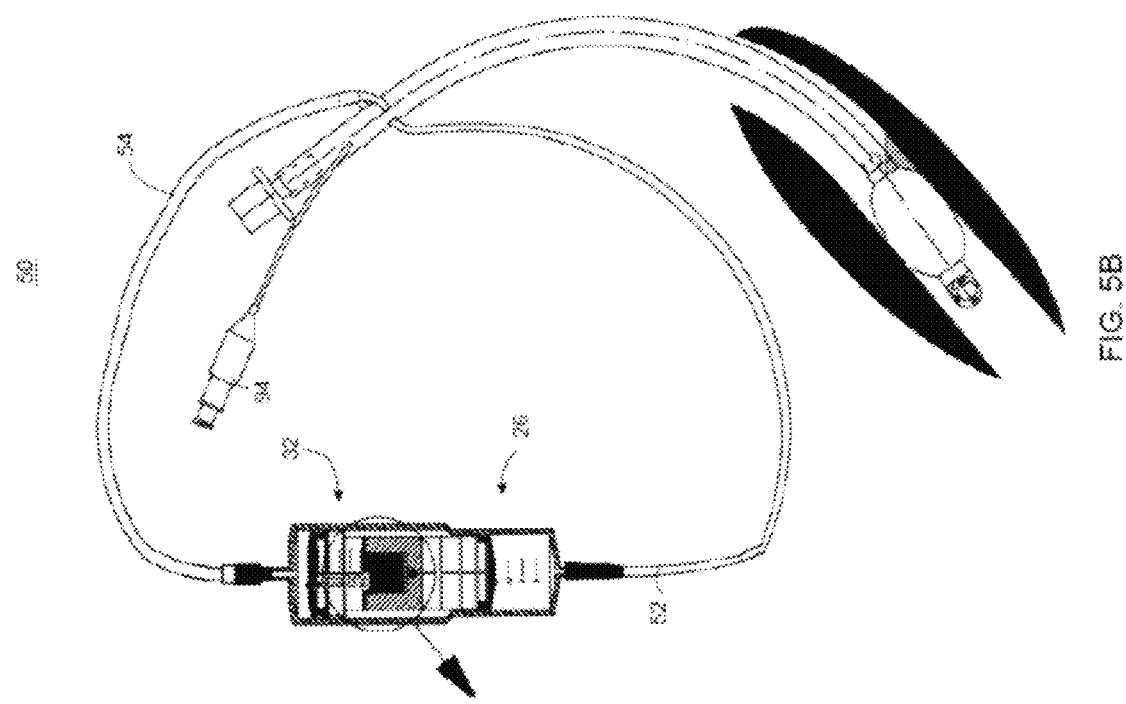
Figure 5A:
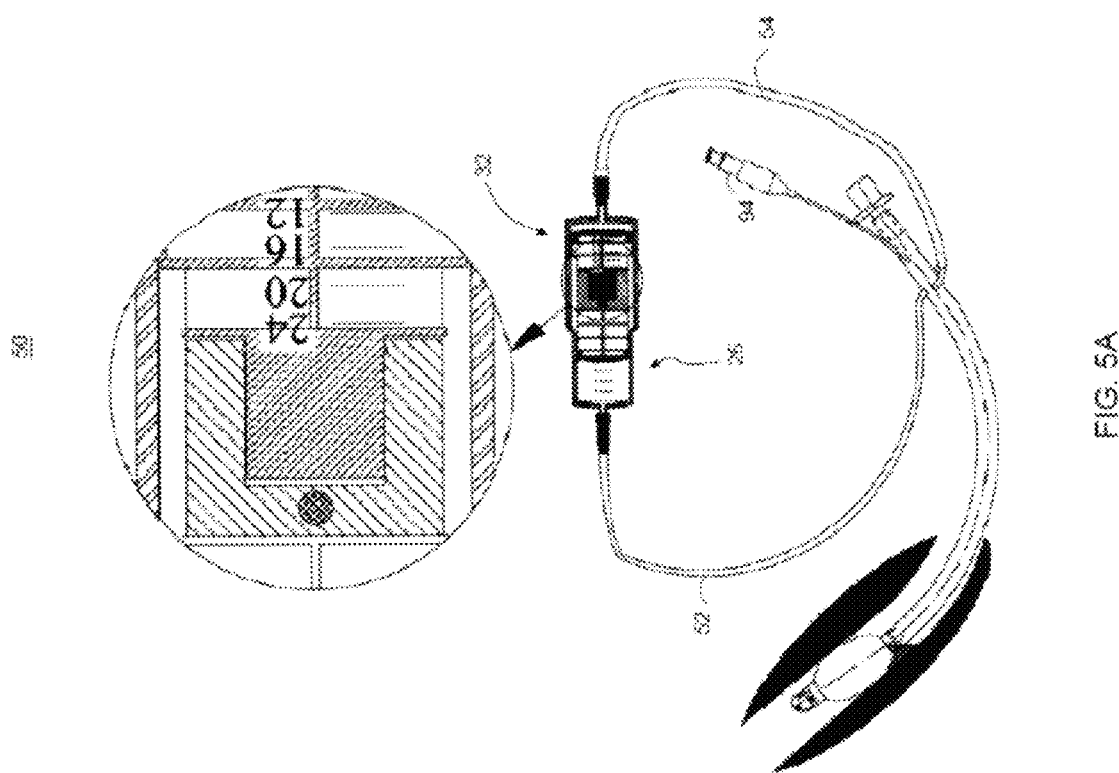
Figure 5F:
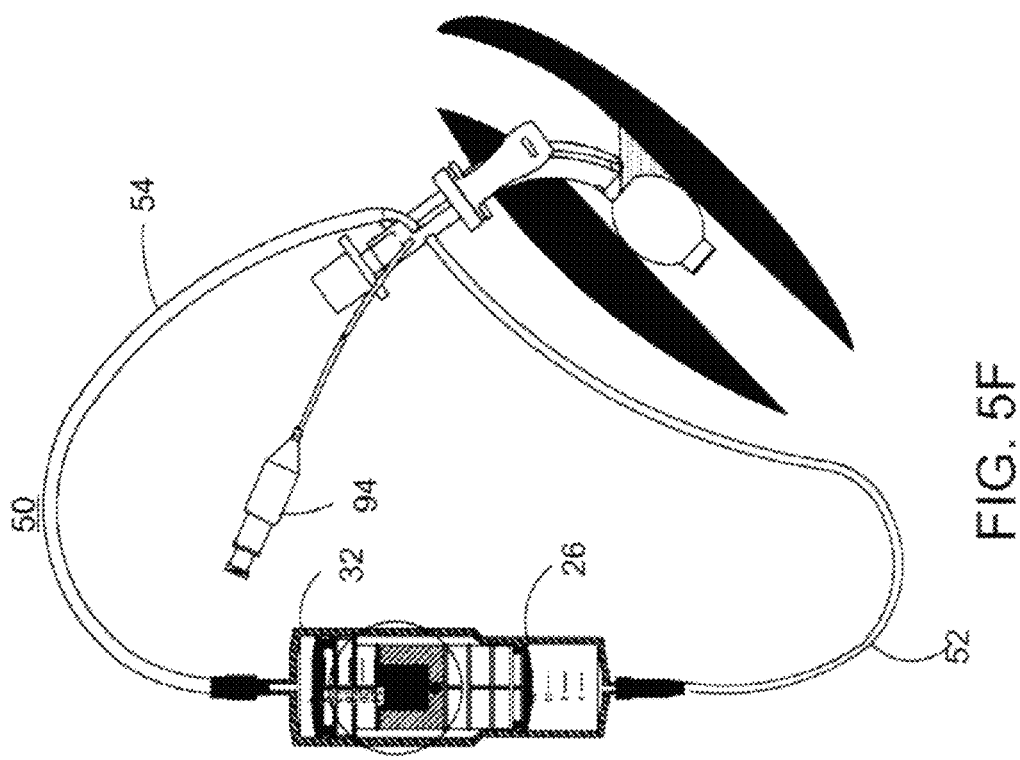
Figure 5E:
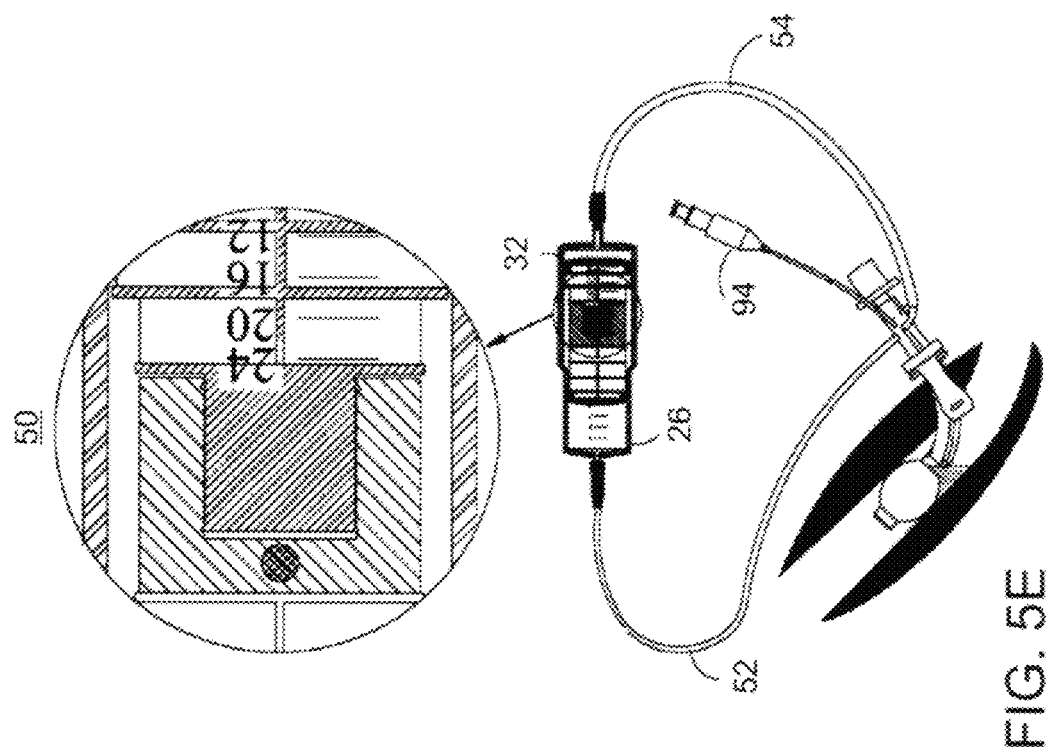
Figure 5G:
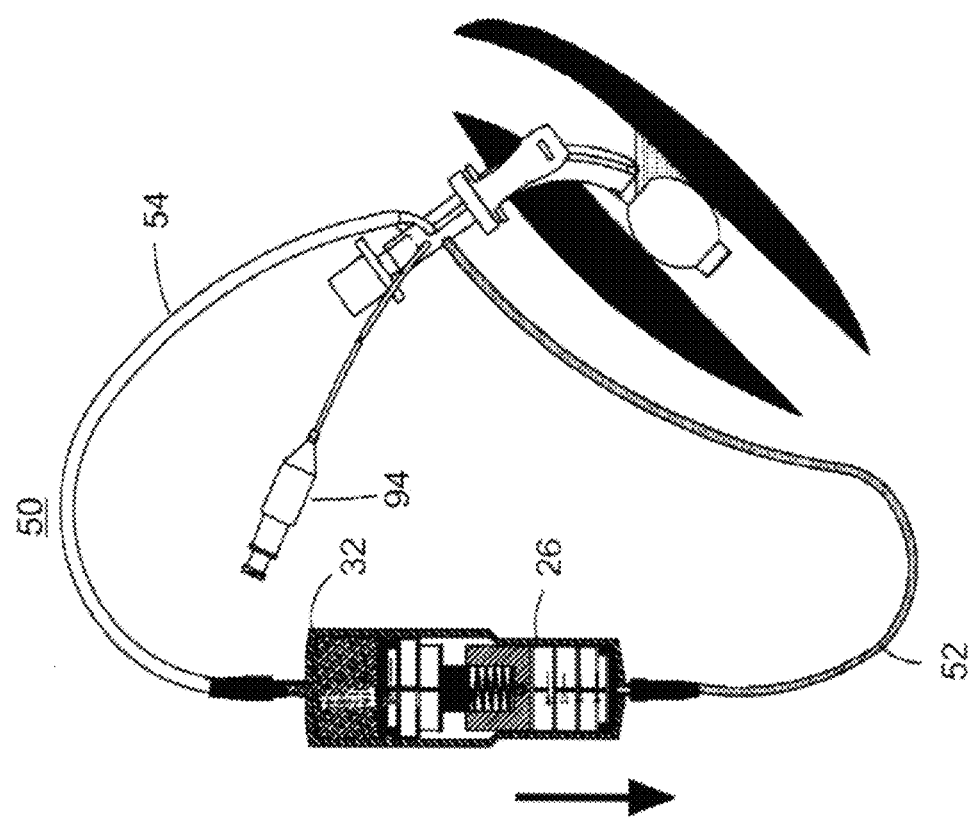
Figure 5H:
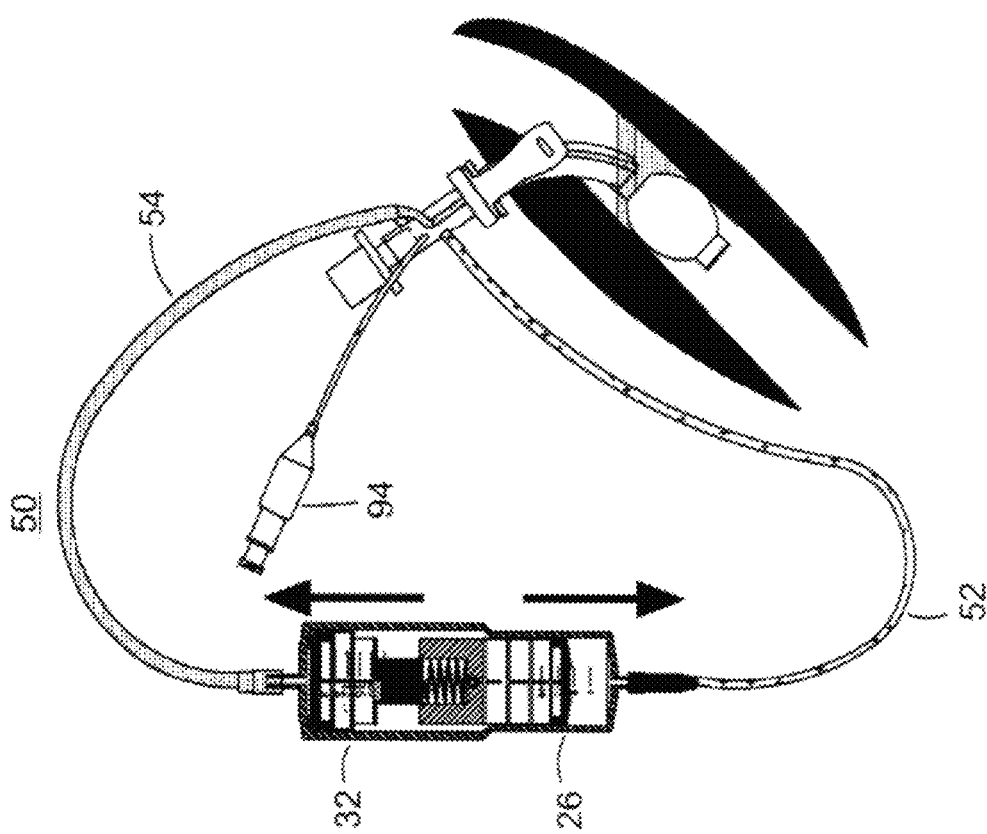

FIGS. 5A-B and 5E-F illustrate system 50 in the initial state. The syringe is filled with, e.g., 4 ml of rinsing solution while the other syringe is filled with, e.g., 12 ml of the same solution, as further detailed hereinabove. Other amounts are not excluded from the scope of the present invention. FIGS. 5C and 5G illustrate a generally simultaneous priming of the suction line and rinsing line by the bidirectional spring and FIGS. 5D and 5H illustrate the simultaneous rinsing (via the rinsing line) and suction (via the suction line).

The configurations described above utilize two syringe-type piston pumps to enable one step irrigation (fluid delivery and concomitant suction). The dual syringe configurations exemplified herein are preferred for their simplicity of design, low cost construction and flexibility and ease of use.

It will be appreciated however, that other configurations utilizing piston type pumps can also be utilized to achieve the same functionality. For example, a configuration which includes crank, cam or cog-wheel driven pistons of opposing or parallel direction (within barrels) can be used to provide concomitant delivery and suction as described above.

Representative examples of several configurations suitable for some embodiments of the present invention are illustrated in FIGS. 6A-G.

FIGS. 6A and 6B are schematic illustrations of device 10 in embodiment of the invention in which device 10 comprises a syringe 62 and a container 64, which is optionally and preferably a bag. Syringe 62 can primarily serve for withdrawing fluid from the body cavity and container 64 can serve for delivering fluid into the body cavity. Thus, container 64 is preferably filled with fluid. Container 64 is preferably a deformable bag, e.g., a disposable bag, which can be made of any material such as polyester, polyethylene terephthalate (PET), copolyethylene terephthalate (CoPET), polybutylene terephthalate (PBT) and the like.

The embodiments in FIGS. 6A and 6B will now be described with reference to FIGS. 6E and 6F.

Figure 6E:
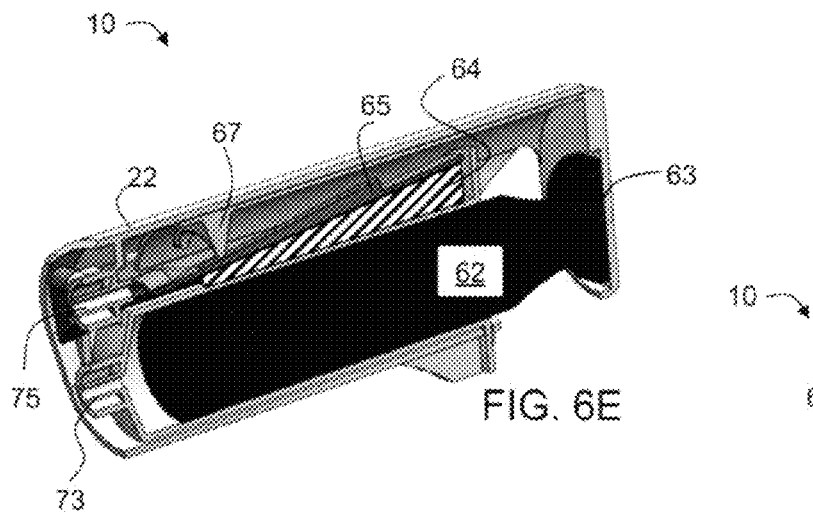

FIG. 6E is a cut view of the embodiment shown in FIG. 6A. Bag 64 is external to syringe 62 but is encapsulated with it in housing 22, within a compartment having a movable oblique element 65. The plunger 63 of syringe 62 comprises or is connected to an extension 67 which engages element 65. When plunger 63 is pulled, syringe 62 withdraws fluid out of the body cavity while at the same time extension 67 slides on oblique element 65 forcing it to apply pressure on bag 64, thereby delivering the fluid out of bag 64, simultaneously with the withdrawal of fluid by syringe 62.

Figure 6F:
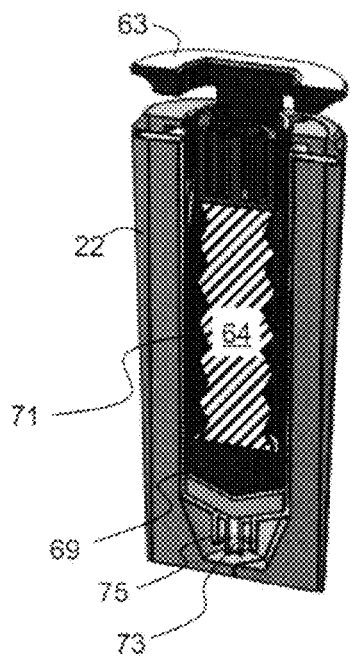

FIG. 6F is a cut view of the embodiment shown in FIG. 6B. Bag 64 is disposed within the barrel 71 of syringe 62, while the plunger 63 is in its pushed position. Bag 64 is disposed such that the tip 69 of plunger 63 is between bag 64 and the nozzle 73 of barrel 71. When plunger 63 is pulled, syringe 62 withdraws fluid out of the body cavity through nozzle 73 while squiring bag 64, thereby delivering the fluid out of bag 64, through a second nozzle 75 which may be disposed laterally to nozzle 73, or, is illustrated in FIG. 6F, circumferential with respect to nozzle 73.

FIG. 6C is a schematic illustration of device 10 in embodiment of the invention in which device 10 comprises two syringes 62 and 66, wherein syringe 66 is a conventional syringe and syringe 62 is a specially designed syringe. This embodiment is better illustrated in FIG. 6G which is a cut view of the embodiment shown in FIG. 6C.

Figure 6G:
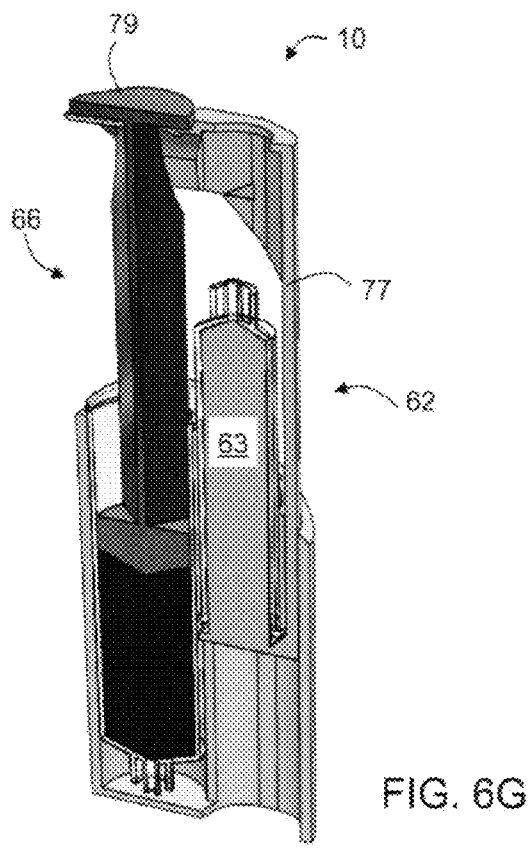

Syringe 62 is filled with fluid (not shown in FIG. 6G). The plunger 63 of syringe 62 is mounted, or being formed, with an extension element 77 than engages the plunger 79 of syringe 66. When plunger 79 is pulled, syringe 66 withdraws fluid out of the body cavity while at the same time element 77 causes plunger 63 to move at the ejecting direction of syringe 62, thereby delivering the fluid out of syringe 62.

FIG. 6D is a schematic illustration of a peristaltic pump 68 which can be used for one or both pumps of device 10. Peristaltic pumps, which are known per se, pump the fluid in a wave-like pattern by sequential deformation and occlusion of several points along the length of a resilient deformable tube 70 which carries the fluid. Operation of such a pump typically involves a mechanical interaction between a portion of resilient tube 70 and a peristaltic mechanism 72 that creates a wave-like deformation along the resilient tube. In various exemplary embodiments of the invention peristaltic pump 68 is manually operated.

Also contemplated, are embodiments in which the device comprises a syringe and a vacuum tube.

FIGS. 7A-E are schematic illustrations of device 10 in embodiments of the invention in which device 10 comprises an actuator member 74, and two piston pumps (shown as syringes 32 and 26) which are arranged within housing 22. In the present embodiments, syringes 32 and 26 are aligned at opposite directions such that the withdrawal direction of one plunger is the same as the ejection direction of the other plunger. The nozzles 126 and 132 of device 10 are optionally and preferably at the same side of housing 22. In these embodiments, fluid communication between the oppositely aligned piston pump (syringe 26 in FIGS. 7A-E) and its respective nozzle (126 in the present example) can be established via an internal conduit generally shown at 87 (FIG. 7D).

Actuator member 74 is preferably a mechanical member, and can be in the form of, for example, a safety hatch or the like. In various exemplary embodiments of the invention member 74 is being operated manually without the use of any other drive means such as an electrical or magnetic motor or an acoustical transducer. Pump 26 and pump 32 are optionally and preferably initially filled with respective initial volumes 76 and 78 of fluid, e.g., irrigation liquid. Typically, volume 76 is 5 ml, and volume 78 is 10 ml, but other amounts are not excluded from the scope of the present invention.

In various exemplary embodiments of the invention member 74 has several modes. A mode of member 74 can be embodied as a position or orientation of member 74 with respect to the static components (e.g., housing 22 of device 10), or as a transition between two positions or orientations.

Member 74 has a first mode (FIG. 7A) in which both pumps are inoperative. In this mode member 74 serves as a safety hatch, and device 10 can be shifted from one location to the other without the risk of accidental operation. In the representative example of FIG. 7A, which is not considered to be limiting, in the first mode, member 74 assumes an orientation which is perpendicular to symmetry axis of the piston pumps. Member 74 also has a second mode in which actuator member activates pump 32 to eject an initial volume 76 of fluid out of the device. In this mode, volume 78 of pump 26 is still filled with fluid. The second mode can be embodied as a transition between two orientations of member 74. For example, the second mode can be utilized by rotating member 74 by 90° to assume an orientation which is generally parallel to the symmetry axis of the piston pumps (FIG. 7B). The rotation generates a force applied by the tip of member 74 on the piston of pump 32, which ejects the fluid in volume 76.

In various exemplary embodiments of the invention member 74 also has a third mode, in which member 74 activates pump 26 to eject an initial portion of the fluid in volume 78 out of the device. Typically, about 2 cc are ejected in the third mode of member 74. Other amounts are not excluded from the scope of the present invention The third mode can be embodied as a transition between two positions of member 74. For example, the third mode can be utilized by pulling member 74 outwardly (see arrow 80) over a preset movement range. A linkage member 82 which is connected to actuator member 74 extends from member 74 to the piston of pump 26. An engaging element 84 at the part of member 82 which is close to pump 26 engages the piston and pushes it in the ejection direction of pump 26, thereby ejecting part of the fluid in volume 78 (FIG. 7C).

In various exemplary embodiments of the invention member 74 also has a fourth mode, in which member 74 simultaneously activates pump 26 to deliver fluid into the body cavity and pump 32 to withdraw fluid from the body cavity. Typically, all the remaining fluid in volume 78 (about 8 cc in the present example) are ejected in the third mode of member 74. The fourth mode can be embodied as a transition between two positions of member 74. For example, the fourth mode can be utilized by pulling member 74 further outwardly (FIG. 7D), over a preset movement range beyond the positioned assumed at the end of the third mode. Engaging element 84 continues to push the piston of pump 26 in its ejecting direction (direction 80 in the present example) while a lever mechanism 86 pulls the piston of pump 32 in its withdrawing direction (in the present example, also direction 80). Thus, in simultaneous manner, fluids enter pump 32 and exit pump 26.

In various exemplary embodiments of the invention member 74 also has a fifth mode, in which member 74 activates only pump 32 to withdraw fluid from the body cavity. The fifth mode can be embodied as a transition between two positions of member 74. For example, the fifth mode can be utilized by pulling member 74 further outwardly (FIG. 7E), over a preset movement range beyond the positioned assumed at the end of the fourth mode. This operation establishes a motion of the piston of pump 32 (via lever mechanism 86) in withdrawing direction 80 thereby facilitating withdrawal of fluids into the device. Since pump 26 does not contain any fluid once member 74 enters its fourth mode, the further pulling of member 74 after the fourth mode does not affect pump 26.

FIGS. 16A-E and 17A-E are schematic illustrations of device 10 in embodiments of the invention in which the pumps are piston pumps embodied as syringes 26 and 32 arranged in housing 22 such that the respective nozzles 126 and 132 are on the same side of device 10, wherein the withdrawing direction of one syringe is the same as the withdrawing direction of the other syringe. In these embodiments, during the phase in which fluid delivery by one syringe is simultaneous with liquid withdrawal by the other syringe, the plungers of the two syringes simultaneously move in opposite directions. FIGS. 16A-E are cross-sectional views, and FIGS. 17A-E are perspective views of device 10 cut open in the lengthwise direction.

The opposite motions of the plungers can be established by means of a cogwheel as further detailed hereinbelow. In the present embodiments, device 10 comprises an actuator member 74 which is preferably a mechanical member, as further detailed hereinabove. For example, member 74 can be in the form of a safety hatch or the like. In various exemplary embodiments of the invention member 74 is being operated manually without the use of any other drive means such as an electrical or magnetic motor or an acoustical transducer. Member 74 can comprise a gripping bar 75 for facilitating its gripping by the operator.

In some embodiments of the present invention one of syringes (syringe 32 in the present example) has a larger barrel diameter than the other syringe (syringe 26 in the present example). The barrel stoke length of the two syringes can be approximately the same. Preferably, the syringe with the smaller diameter is used only for delivering fluid to the body cavity, while the syringe with the larger diameter is first used to deliver an initial amount of fluid to the body cavity and thereafter used for withdrawing fluid from the body cavity.

Typical dimensions for the barrel of syringe 32 is from about 90 to about 100 mm (e.g., about 95 mm) in stroke length and from about 20 to about 26 mm (e.g., about 23 mm) in internal diameter. Typical dimensions for the barrel of syringe 26 is from about 45 to about 60 mm (e.g., about 52 mm) in stroke length and from about 10 to about 20 mm (e.g., about 15 mm) in internal diameter.

Both syringes 32 and 26 are optionally and preferably initially filled with respective initial volumes 76 and 78 of fluid (FIG. 16A), e.g., irrigation liquid. Typically, volume 76 is 5 ml, and volume 78 is 10 ml, but other amounts are not excluded from the scope of the present invention.

In the present embodiments of the invention member 74 has several modes. As explained above, a mode of member 74 can be embodied as a position or orientation of member 74 with respect to the static components (e.g., housing 22 of device 10), or as a transition between two positions or orientations.

Member 74 has a first mode (FIGS. 16A and 17A) in which both syringes are inoperative. In this mode member 74 serves as a safety hatch, and device 10 can be shifted from one location to the other without the risk of accidental operation. In the representative example of FIG. 16A, which is not considered to be limiting, in the first mode, member 74 assumes an orientation which is perpendicular to symmetry axis of the syringes.

Figure 16A:
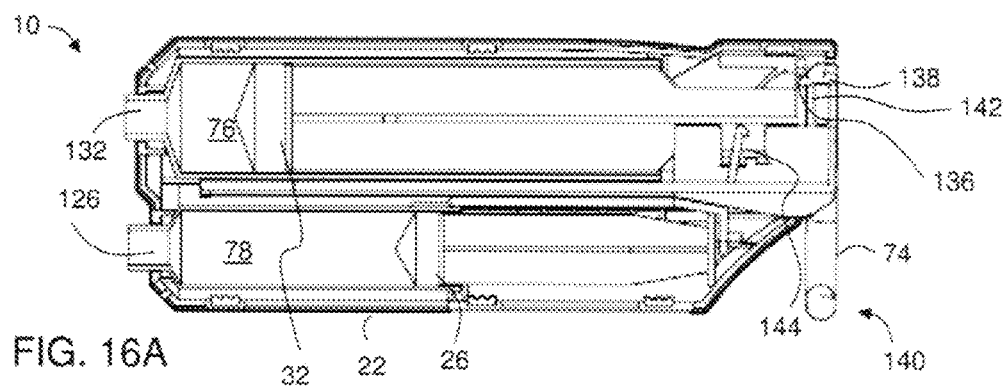
Figure 16B:
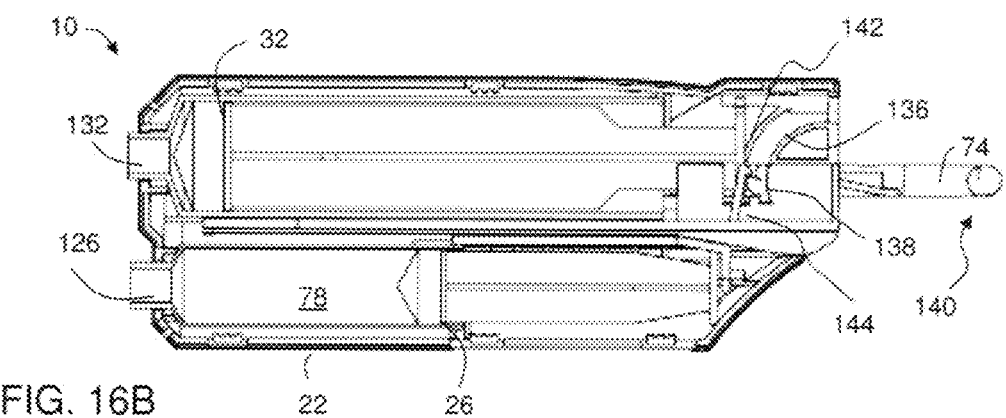
Figure 17A:
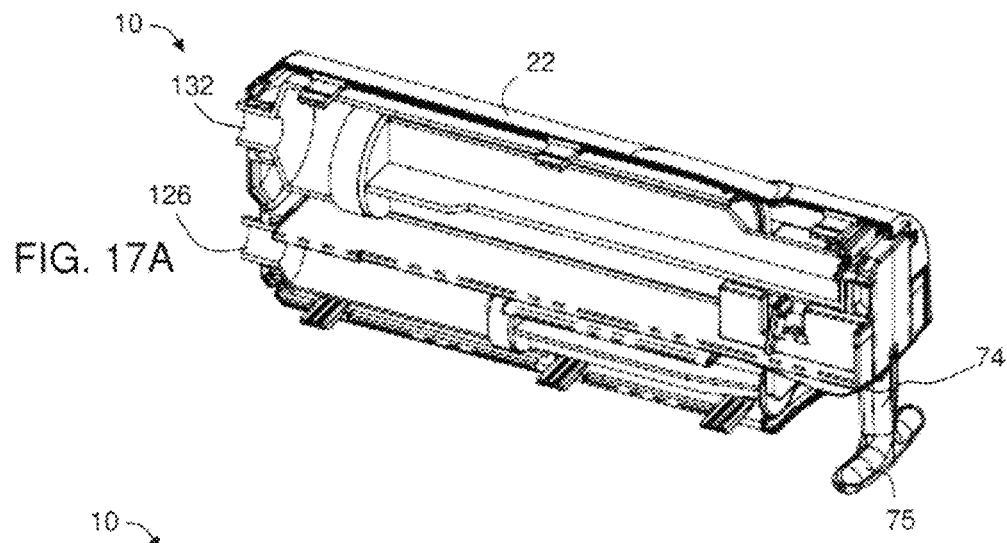
Figure 17B:
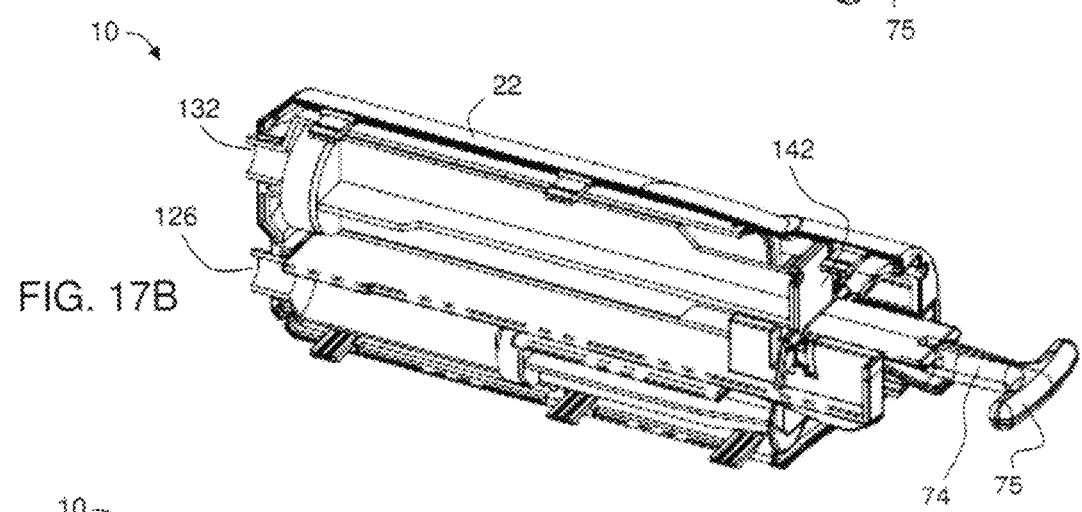

Member 74 also has a second mode in which actuator member 74 activates syringe 32 to eject initial volume 76 of fluid out of the device. In this mode, volume 78 of pump 26 is still filled with fluid. The second mode can be embodied as a transition between two orientations of member 74. This is illustrated in FIGS. 16B and 17B. As shown, member 74 is rotated by 90° to assume an orientation which is generally parallel to the symmetry axis of the piston pumps. Optionally and preferably housing 22 of device 10 is provided with a guiding track 136 having a shape of a quarter of a circle, for guiding the distal end 138 of member 74 while the operator rotates its proximal end 140. The plunger of syringe 32 is preferably provided with a plate 142 engaged by distal end 138 such that the rotation of member 74 along track 136 pushes the plunger of syringe 32 forward to eject the fluid in volume 76 out of nozzle 132.

In various exemplary embodiments of the invention hosing 22 comprises a locking mechanism 144 configured for locking member 74 in its parallel orientation, once member completes its rotation along track 136. In the representative illustration of FIGS. 16A-E, locking mechanism 144 operates according to the principles of a ratchet. Specifically, distal end 138 is formed with a recess and locking mechanism 144 is in the form of a lever having a tooth which is compatible with the recess of distal end 138. Once member 74 completes its rotation along track 136 the lever is biased against the recess and prevents member 74 from rotating backward thereby locking it at its parallel orientation.

In various exemplary embodiments of the invention member 74 also has a third mode, in which member 74 activates syringe 26 to eject the initial portion of the fluid in volume 78 out of nozzle 126. Typically, about 2 ml are ejected in the third mode of member 74. Other amounts are not excluded from the scope of the present invention.

Figure 16C:
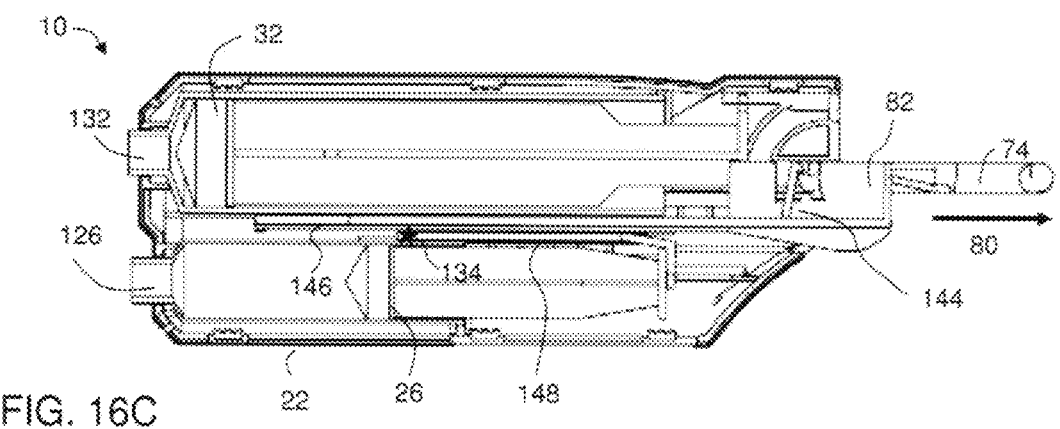

The motion of syringe 26 is established by means of a cogwheel in a manner that will now be explained. Referring to FIG. 16C, a first linear transmission element 146 is connected to member 74 and extends from member 74 inwardly into housing 22. For example, element 146 can extend to the barrel of syringe 26. A second linear transmission element 148 is connected to the plunger of syringe 26, and extends along the plunger but external to the barrel of syringe 26. Transmission elements 146 and 148 are spaced apart and generally parallel to each other and to the plungers of the syringes. Transmission elements 146 and 148 can be, for example, racks or chains. A cogwheel 134 is mounted with its central axis of rotation fixed onto housing 22 between elements 146 and 148, such that the cogwheel 134 engages transmission elements 146 and 148 in an antipodal manner. Thus, motion of element 146 in one direction establishes rotary motion of cogwheel 134 which in turn drives element 148 to move in the opposite direction.

Figure 17C:
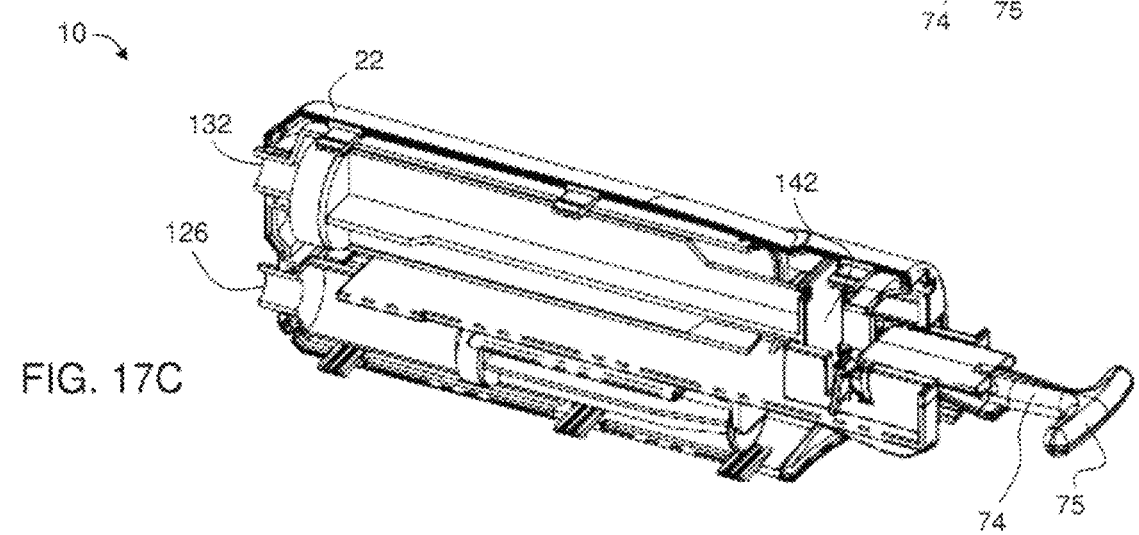

The third mode can be embodied as a transition between two positions of member 74. This is schematically illustrated in FIGS. 16C and 17C. While being locked in its parallel orientation, member 74 is pulled outwardly in a direction indicated by arrow 80 over a preset movement range. Element 146 moves together with member 74 and establishes rotary motion of cogwheel 134. The rotation of cogwheel 134 establishes translation motion of element 148, hence also of the plunger of syringe 26 in the opposite direction. In the third mode, the plunger of syringe 32 preferably remains at its forward position without moving.

In various exemplary embodiments of the invention member 74 also has a fourth mode, in which member 74 simultaneously activates syringe 26 to deliver fluid into the body cavity and syringe 32 to withdraw fluid from the body cavity.

Figure 17D:
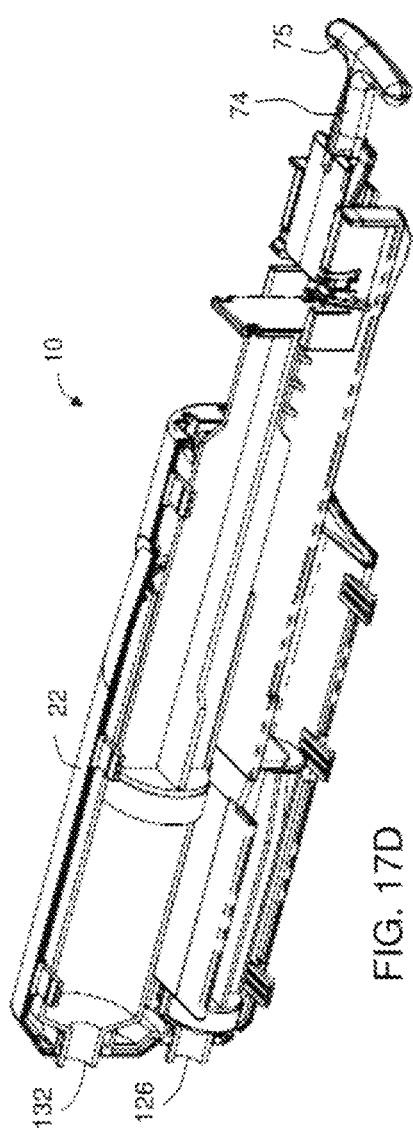
Figure 17E:
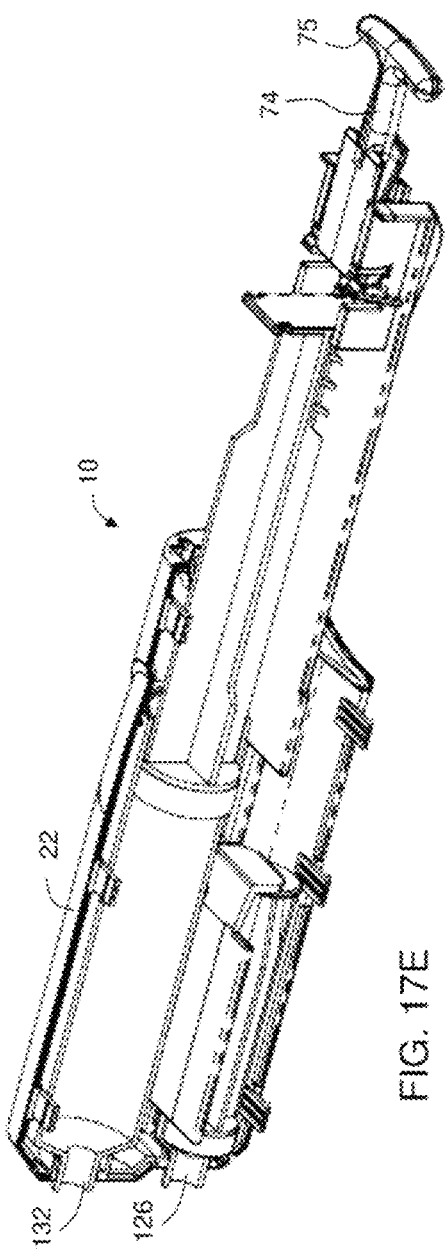

The fourth mode can be embodied as a transition between two positions of member 74. This is schematically illustrated in FIGS. 16D and 17D. Member 74 is optionally and preferably connected to a linkage member 82 which is preferably disengaged from the plunger of syringe 32 during the third mode of member 74 (until the completion of the aforementioned transition between the two respective positions). The fourth mode can be utilized by pulling of member 74 further outwardly over a preset movement range beyond the positioned assumed at the end of the third mode. Such further pulling brings linkage member 82 into engagement with the plunger of syringe 32 so that the motion of member 74 outwardly (beyond the third mode) is also accompanied by motion of the plunger of syringe 32 in its withdrawing direction. The plunger of syringe 32, in turn, pulls the first transmission member 146 which continues to rotate cogwheel 134. Still engaging second transmission member 148, cogwheel 134 establishes motion of member 148 hence also of the plunger of syringe 26 in the opposite direction.

Thus the fourth mode features a simultaneous withdrawal and delivery operation, wherein syringe 32 withdraws fluid through nozzle 132 and syringe 26 delivers fluid through nozzles 126. Typically, once the transition to the fourth mode is completed, all the remaining fluid in the barrel of syringe 26 (about 8 ml in the present example) is ejected. Preferably, in these embodiments, the length of first transmission member 148 is sufficiently short such that, at the end of the transition from the third mode to the fourth mode, the first transmission member 146 is disengaged from cogwheel 134.

In various exemplary embodiments of the invention member 74 also has a fifth mode, in which member 74 activates only syringe 32 to withdraw fluid from the body cavity. The fifth mode can be embodied as a transition between two positions of member 74, as schematically illustrated in FIG. 16E. Member 74 is pulled further outwardly over a preset movement range beyond the positioned assumed at the end of the fourth mode. This operation establishes a motion of the plunger of syringe 32 (via linkage member 82) in withdrawing direction 80 thereby facilitating withdrawal of fluids via nozzle 132 into the device. Since cogwheel 134 is at this stage disengaged from the first transmission member 146, the motion of member 146 is not accompanied by rotation of the cogwheel, so that there is no motion of the plunger of syringe 26 during this operation.

A device 10 which includes actuator member 74 (such as the device illustrated in FIGS. 7A-E, 16A-E or 17A-E), can be implemented in system 50 described above. FIGS. 8A and 8B are schematic illustration of system 50 in embodiments of the present invention in which device 10 including member 74 is connected to tube 60. FIG. 8A show system 50 in embodiments in which tube 60 is adapted for being introduced into the trachea (either orally or in a tracheostomy procedure), and FIG. 8B shows system 50 in embodiments in which tube 60 is adapted for being inserted into the ear canal. The skilled person, provided by the details provided herein, will know how to adjust the drawings for embodiments in which tube 60 is introduced into other cavities, e.g., the intestines.

Reference is now made to FIGS. 9A and 9B which are schematic illustrations of device 10 in embodiments of the invention in which device 10 comprises an analog (FIG. 9A) or digital (FIG. 9B) pressure measuring device 90. Device 90 can be mounted, for example, onto housing 22 of device 10. Device 90 comprises an inlet 92 which can be connected, for example, to the cuff inflation line of tube 60 (not shown, see 94 in FIGS. 2A-J, 4A-J, 5A-H and 8A), for determining the inflation pressure of the cuff. This embodiment is particularly useful when the intubated subject is connected to a ventilation or anesthetic machine which does not provide indication of cuff inflation pressure. Measuring device can be of any type known in the art, including, without limitation, a device incorporating a pressure sensor, e.g., a piezoelectric or a piezoresistive element, a manometer, e.g., a capacitance manometer, a mercury manometer, a flow meter, and the like.

The device of the present embodiments may, if desired, be presented in a pack, such as an FDA-approved kit. The pack may, for example, comprise metal or plastic foil, such as a blister pack. The pack may be a disposable pack. The pack may be accompanied by instructions for administration. The pack may also be accompanied by a notice in a form prescribed by a governmental agency regulating the manufacture, use, or sale of pharmaceuticals, which notice is reflective of approval by the agency of the form of the compositions for human or veterinary administration. Such notice, for example, may include labeling approved by the U.S. Food and Drug Administration for prescription drugs or of an approved product insert.

A representative example of a pack according to some embodiments of the present invention is illustrated in FIG. 10. Showing a pack 100 with two devices 10. For example, the device shown in FIG. 7A-F can be installed within an automatic syringe pump that replaces the manual activation by configured external electric piston that pulls the safety hatch and draws the evacuation plunger in a programmed mode. The automatic device can include one or more devices connected to same lumens.

The device of the present embodiments optionally and preferably includes therein one or more types of substances that are capable of providing indication of presence of a disease. Preferably, the substance or substances are incorporated in the pump that serves for withdrawing fluid from the body cavity. The substance can change its property, for example, optical property (e.g., color) when contacted with diseased secretions. The substance can comprise for example, a functional group that react with the disease of interest and provides indication of its existence. The substance can also be a biological marker, such as, but not limited to, cells, proteins, enzymes, nucleic acids, carbohydrate markers, cell surface markers, circulating antibodies, secretory antibodies, cell-associated antibodies, intracellular markers, morphological markers, functional parameters (e.g. enzymatic activity), pH, cytokines and chemokines, viral markers, bacteria, fungi, protozoa, nematodes and parasites.

Reference is now made to FIGS. 18A-B which are schematic illustrations of a kit 200, according to some embodiments of the present invention. Kit 200 can comprise a device, such as device 10 described above, and an intubation device 102 adapted for being introduced into the body cavity, wherein each of the pumps of device 10 is connectable to a separate fluid line of the intubation device.

FIG. 18A shows an external planar view of kit 200 once device 10 is connected to intubation device 102, and FIG. 18B shows a cross-section in a plan along line A-A of FIG. 18A.

Tube device 102 can comprise a tubular wall 206 defining a main lumen 104, and an inflatable cuff 210 disposed circumferentially around wall 206 near the distal end 214 of device 102. Wall 206 has a dorsal side and a ventral side. In use, device 102 is introduced into the subject's trachea (not shown) such that the dorsal and ventral sides of wall 206 respectively face the dorsal and ventral sides of the trachea.

Embedded in wall 206 are two dorsal lumens 204 and 205 at the dorsal side, a ventral lumen 216 at the ventral side, and a cuff inflation lumen 212 (FIG. 18B). Lumen 212 can be formed at any location on the perimeter of wall 206. For example, in the illustration of FIG. 18B lumen 212 is between the ventral and dorsal sides of wall 206. In some embodiments of the present invention lumens 204 and 205 are disposed symmetrically at both sides of the sagittal plane 228, passing through lumen 216 at a cross-section perpendicular to the longitudinal axis of main lumen.

Each of dorsal lumens 204, 205 and ventral lumen 216 has a distal opening above cuff 210. Lumens 204, 205 and 216 can terminate above the cuff 210 or they can extend until the distal end 214. In the latter embodiment, lumens 204, 205 and 216 are preferably closed (e.g., welded) at distal end 214. The distal opening of ventral lumen 216 is shown at 218. The distal opening of dorsal lumen 204 is indicated by reference numeral 220. The ordinarily skilled person, provided with the details described herein would know how to locate the distal openings of dorsal lumen 205. Typically, the distal openings of lumens 204 and 205 are at opposite sides of sagittal plane 228 of the tube. In some embodiments, inserts are introduced into one or more of openings 218, 220 and/or the opening of lumen 205 in the direction of distal end 214, so as to close the respective lumen(s) also immediately below these openings.

In various exemplary embodiments of the invention device 102 comprises at least a first fluid line 106a, a second fluid line 106b and a cuff inflation line 106c. Each of lumens 204, 205 and 216 is in fluid communication with a fluid line of device 102. In various exemplary embodiments of the invention ventral lumen 216 is in fluid communication with line 106a, cuff inflation lumen 212 is in fluid communication with line 106c and both dorsal lumens 204 and 205 are in fluid communication with line 106b. As shown, line 106b is split into two fluid lines each leading to one of lumens 204 and 205.

Once kit 200 is assembled for use, nozzle 132 of device 10 can be connected to fluid line 106b and nozzle 126 can be connected to fluid line 106a. Configurations in which nozzle 132 is connected to fluid line 106a and nozzle 126 is connected to fluid line 106b are not excluded from the scope of the present invention.

According to some embodiments of the present invention there is provided a method suitable for irrigating a body cavity with fluid. Generally, the method comprises manually delivering a first volume of fluid to the body cavity, and manually delivering a second volume of the fluid and simultaneously withdrawing at least second volume of the fluid from the body cavity. The method can be effected, for example, by a device that includes manually-operated pump mechanism as further detailed hereinabove, e.g., device 10. In various exemplary embodiments of the invention the method employs kit 200.

In various exemplary embodiments of the invention the method delivers fluid is at volumetric flow rate $Q_1$, and simultaneously withdraws fluid at volumetric flow rate $Q_2$, wherein there is a linear relation between $Q_1$ and $Q_2$, as further detailed hereinabove.

The method is optionally and preferably executed using a device which is connected to the body cavity via a tube having a first line in fluid communication with the first pump of the device and a separate second line in fluid communication with the second pump of the device. The following protocol is preferably, but not necessarily employed. The second pump is operated to deliver fluid into the second line, so as to at least fill second line. The first pump is operated to deliver fluid into the first line, so as to at least fill first line. Once the lines are filled, the first pump is operated to withdraw fluid from the first line and the second pump is simultaneously operated to deliver fluid into the second line. Subsequently, the first pump is operated to withdraw fluid from the first line while the second pump remains inoperative.

As used herein the term "about" refers to ±10%.

The word "exemplary" is used herein to mean "serving as an example, instance or illustration." Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments." Any particular embodiment of the invention may include a plurality of "optional" features unless such features conflict.

The terms "comprises", "comprising", "includes", "including", "having" and their conjugates mean "including but not limited to".

The term "consisting of means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", an and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

A prototype MASS device and an FDA/CE approved endotracheal tube device were manufactured and tested according to some embodiments of the present invention. The prototype MASS device and the endotracheal tube are illustrated in FIGS. 11A-B.

The prototype MASS device included two opposingly mounted syringes with their plungers linked such that they can operate simultaneously, as described in greater detail above.

The endotracheal tube device included a main lumen, two suction lumens embedded in the wall of the main lumen at the dorsal side of the tube with distal openings above the cuff, and an irrigation lumen embedded in the wall of the main lumen at the ventral side of the tube and having an opening above the cuff. The embedded suction lumens were unified to one external lumen. A cross section of the tube is illustrated in FIG. 11B.

Material and Methods

Experiment 1

Evacuation of Secretions using of the Prototype MASS device

A goat was anesthetized (Ketamine and Isofluran) and intubated with the endotracheal tube. Sealing was validated by above cuff $CO_2$ reading, as disclosed, for example, in Efrati, M D et al., "Optimization of Endotracheal Tube Cuff Filling by Continuous Upper Airway Carbon Dioxide Monitoring," Anesth. Analg; vol. 101, pp. 1081-1088 (2005). $CO_2$ was monitored through the vent lumen of the tube. A partial $CO_2$ pressure of less than 1 mmHg, was considered as indicative of adequate sealing.

Contrast medium (OMNIPAQUE-IOHEXOL 350 mgI/ml) was used for simulation of above cuff fluid. 5 ml of contrast medium were injected via the suction lumen under fluoroscopy recording.

The prototype MASS device was used for synchronized irrigation and suction. 10 ml of Saline were used for irrigation. The entire irrigation/suction procedure was monitored and recorded by fluoroscopy. The amount of the evacuated fluids were measured and recorded.

The above procedure was repeated with following cuff pressures of 45, 40, 35, 30, 25, 20, 15, 10 and 5 mmHg. At 5 mmHg a leakage above the cuff was detected by above cuff $CO_2$ readings.

Experiment 2

Evacuation of Secretions Using Conventional Technique (Rinsing Followed by Suction)

In this experiment the same endotracheal tube (FIG. 11) was used. The cuff pressure was set to 20 mmHg and the ealing was validated by above cuff $CO_2$ as described above. Contrast medium (OMNIPAQUE-IOHEXOL 350 mgI/ml) was used for simulation of above cuff fluid/secretions: 5 ml of contrast medium were injected via the suction lumen. 10 ml of saline were injected via the suction lumen. Secretions were evacuated using a 20 ml syringe. The amount of the evacuated fluids were measured and recorded.

The experiment was repeated for the following cuff pressures: 15, 10, and 5 mmHg. At 5 mmHg a leakage above the cuff was detected by above cuff $CO_2$ readings.

Experiment 3

Evacuation of Secretions Using a Conventional Hi-Lo® Evac Tube

The goat was intubation with a Hi-Lo Evac endotracheal tube (I.D 8.0 Polyurethane cuff; Evac, Mallinckrodt, USA). The cuff pressure was set to 20 mmHg and sealing was validated by above cuff $CO_2$ reading as further detailed hereinabove. The $CO_2$ readings were done through the suction lumen. Contrast medium (OMNIPAQUE-IOHEXOL 350 mgI/ml) was used for simulation of above cuff fluid/secretions. 5 ml of contrast medium were injected via the suction lumen under fluoroscopy recording. 10 ml of saline were injected via the suction lumen. Secretions were evacuated with a 20 ml Syringe. The entire irrigation/suction procedure was monitored and recorded by fluoroscopy. The amount of the evacuated fluids were measured and recorded. The experiment was repeated with the following cuff pressure 20, 15, 10 and 5 mmHg.

Results

The results of Experiment 1 are summarized in Table 1.

TABLE 1

| | Experiment 1 | | | |
|---|---|---|---|---|
| Test | Cuff pressure (mmHg) | Fluid leakage into lung detection (Y/N) | Fluid Evacuated (ml) | CO2 (mmHg) |
| 1 | 45 | N | 15 | 0.8 |
| 2 | 40 | N | 15 | 0.9 |
| 3 | 35 | N | 15 | 0.6 |
| 4 | 30 | N | 15 | 0.54 |
| 5 | 25 | N | 16 | 0.7 |
| 6 | 20 | N | 15 | 0.6 |
| 7 | 15 | N | 15 | 0.55 |
| 8 | 10 | N | 17 | 0.5 |
| 9 | 5 | Y | 11 | 7.43 (max) |
| 10 | 5 | Y | 13 | 7.43 (max) |

FIG. 12 is a fluoroscopy image of the goat's trachea with the endotracheal tube of the present embodiments before the evacuation of the secretions. The secretions (dark regions) and cuff (central region) are bordered on the image.

FIG. 13 is a fluoroscopy image of the goat's trachea with the endotracheal tube after the evacuation of the secretions using the prototype MASS device of the present embodiments. As shown, the secretions have been removed by their entirety.

Table 1 and FIGS. 12 and 13 demonstrate that after the MASS procedure (Experiment 1) no leakage around the cuff was detected by fluoroscopy and the whole amount of fluids that were rinsed and the amount of contrast medium were aspirated. The prototype MASS device of the present embodiments with its related synchronized rinsing/suction procedure assured a comprehensive evacuation of secretions from above the cuff.

The results of Experiment 2 are summarized in Table 2.

TABLE 2

| | Experiment 2 | | | |
|---|---|---|---|---|
| Test | Cuff pressure (mmHg) | Fluid leakage into lung detection (Y/N) | Fluid Evacuated (ml) | CO2 (mmHg) |
| 11 | 20 | N | 15 | 0.78 |
| 12 | 15 | N | 15 | 0.6 |
| 13 | 10 | N | 15 | 0.6 |
| 14 | 5 | Y | 2 | 7.43 |

Table 2 demonstrates that employing rinsing followed by suction in the endotracheal tube resulted in complete evacuation of secretions above the cuff.

The results of Experiment 3 are summarized in Table 3.

TABLE 3

| | Experiment 3 | | | |
|---|---|---|---|---|
| Test | Cuff pressure (mmHg) | Fluid leakage into lung detection (Y/N) | Fluid Evacuated (ml) | CO2 (mmHg) |
| 15 | 20 | N | 11 | 0.5 |
| 16 | 20 | N | 11 | 0.5 |
| 17 | 15 | N | 12 | 0.7 |
| 18 | 10 | N | 13 | 0.6 |
| 19 | 5 | N | 11 | 0.7 |

FIG. 14 is a fluoroscopy image of the goat's trachea with the Hi-Lo® Evac tube before the evacuation of the secretions. The secretions (dark regions) and cuff (central region) are bordered on the image.

FIG. 15 is a fluoroscopy image of the goat's trachea with the Hi-Lo® Evac tube after the evacuation of the secretions by rinsing followed by suction. The secretions (dark regions) and cuff (central region) are bordered on the image.

Table 3 and FIGS. 14 and 15 demonstrate that employing rinsing followed by suction in the Hi-Lo® Evac tube resulted in only partial evacuation of secretions leaving diluted secretions above the cuff at the end of the procedure.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A device for irrigating a body cavity, the device comprising:
   a first pump and a second pump being operatively linked via a manually-operated actuator member having a handle,
   wherein said actuator member has at least a mode in which a motion of said handle activates only said first pump and a mode in which a motion of said handle simultaneously activates both said first and said second pumps,
   wherein in said mode in which said motion of said handle activates only said first pump, said first pump ejects an initial volume of fluid out of the device, and
   wherein in said mode in which said motion of said handle simultaneously activates both said first pump and said second pumps, said second pump ejects fluid out of the device and said first pump withdraws fluid into the device.

2. The device according to claim 1, wherein said actuator member additionally has a mode in which said actuator member activates only said first fluid pump to withdraw fluid from the body cavity.

3. The device according to claim 2, wherein said mode in which said actuator member simultaneously activates said first and said second pumps corresponds to a linear motion of said actuator member in a first direction, and wherein said mode in which said actuator member activates only said first fluid pump to withdraw fluid from the body cavity also corresponds to motion of said actuator member in a first direction.

4. The device according to claim 1, wherein said actuator member additionally has a mode in which both said pumps are inoperative.

5. The device of claim 1, wherein said first pump is configured to withdraw fluid to the body cavity at a first volumetric flow rate and said second pump is configured to withdraw fluid from the body cavity at a second volumetric flow rate, and wherein there is a linear relation between said first and said second volumetric flow rates.

6. The device according to claim 1, wherein said first pump is a first piston pump having a first piston, and said second pump is a second piston pump having a second piston.

7. The device of claim 6, wherein said first piston and said second piston are linked in a manner which enables independent movement of said first piston and said second piston through a preset movement range, and linked movement of said first piston and said second piston beyond said preset movement range.

8. The device according to claim 7, wherein movement of said first piston within said preset movement range delivers a first volume of fluid to the body cavity and further wherein movement of said second piston beyond said preset movement range delivers a second volume of fluid and operates said first piston to withdraw at least said second volume of fluid.

9. The device according to claim 6, wherein said piston pumps are aligned parallel to each other such that a withdrawing direction of said first piston pump is parallel to an ejecting direction of said second piston pump.

10. The device according to claim 9, further comprising a cogwheel configured for linking between a motion of said actuator member and a motion of said second piston.

11. The device according to claim 10, further comprising a first linear transmission element connected to said actuator member and configured to move together with said actuator member over a movement range selected such that said cogwheel engages said first linear transmission element over part of said range.

12. The device according to claim 11, further comprising a second linear transmission element connected to said piston of said second pump, wherein said cogwheel engages said second linear transmission element, such that linear motion of said second linear transmission element is established by rotary motion of said cogwheel.

13. The device according to claim 6, wherein said piston pumps are aligned parallel to each other such that a withdrawing direction of said first piston pump is opposite to an ejecting direction of said second piston pump.

14. The device according to claim 6, wherein said actuator member comprises a rotatable safety hatch configured to engage said first pump while rotating from a first orientation to a second orientation so as to activate said first pump to eject said initial volume of fluid, wherein while said safety hatch is at said first orientation both said pumps are inoperative.

15. The device according to claim 1, wherein at least one of said first and said second pumps is a peristaltic pump.

16. The device according to claim 1, wherein said first pump is a container having an under pressure therein.

17. The device according to claim 1, wherein said second pump is a deformable bag.

18. The device according to claim 1, further comprising a pressure measuring device.

19. The device according to claim 1, wherein at least one of said first and said second pumps comprises a biomarker therein.

20. A kit, comprising the device according to claim 1, and intubation device adapted for being introduced into the body cavity, wherein each of said first and said second pumps is connectable to a separate fluid line of said intubation device.

21. The kit according to claim 20, wherein said intubation device comprises:
   a flexible tubular body being adapted for being introduced into the trachea of a subject and having a wall defining a main lumen; and
   an inflatable cuff associated with said tubular body and arranged to be located at a location in the patient trachea;
   said wall being embedded with at least:
   (i) two suction lumens with respective openings above said cuff, said openings being arranged laterally with respect to each other within said wall,
   (ii) a cuff inflation lumen with opening at said cuff, and
   (iii) an irrigation lumen with opening above said cuff.

22. The kit according to claim 21, wherein said wall has a dorsal section and a ventral section at opposite sides of a longitudinal axis of said tubular body, and wherein said openings of said suction lumens are both located at said dorsal section.

23. The kit according to claim 21, wherein said wall has a dorsal section and a ventral section at opposite sides of a longitudinal axis of said tubular body, and wherein said opening of said irrigation lumen is located at said ventral section.

24. The kit according to claim 21, wherein said suction lumens are unified to a single fluid line external to said tubular body.

25. The kit according to claim 20, wherein said intubation device is adapted for intubation selected from the group consisting of oral endotracheal intubation and tracheostomy intubation.

26. A method of irrigating a body cavity with fluid, the method comprising:
(a) moving a handle of an irrigation device to manually deliver a first volume of fluid to the body cavity, without withdrawing fluid from the body cavity; and, subsequently,
(b) moving said handle to: (i) manually deliver a second volume of the fluid, and (ii) simultaneously withdrawing at least said second volume of the fluid from the body cavity;
wherein said device comprises a first pump and a second pump operatively linked via a manually-operated actuator member having said handle,
wherein said device is connected to the body cavity via a tube having a first line in fluid communication with said first pump and a separate second line in fluid communication with said second pump, wherein the method comprises:
moving said handle to operate said second pump to deliver fluid into said second line, so as to at least fill said second line;
moving said handle to operate said first pump to deliver fluid into said first line, so as to at least fill said first line; and
moving said handle to simultaneously said first pump to withdraw fluid from said first line and said second pump to deliver fluid into said second line.

27. The method according to claim 26, further comprising subsequently to said (b), withdrawing fluid from the body cavity without delivering fluid into the body cavity.

28. The method according to claim 26, wherein the body cavity is the trachea.

29. The method according to claim 26, wherein the body cavity is the trachea and the method is executed during a procedure selected from the group consisting of oral endotracheal intubation and tracheotomy.

30. The method according to claim 26, wherein the body cavity is selected from the group consisting of the ear canal and the intestines.

31. A method of irrigating a body cavity with fluid, the method comprising:
(a) moving a handle of an irrigation device to manually deliver a first volume of fluid to the body cavity, without withdrawing fluid from the body cavity;
(b) subsequently to (a), moving said handle to: (i) manually deliver a second volume of the fluid, and (ii) simultaneously withdrawing at least said second volume of the fluid from the body cavity; and
(c) subsequently to (b), withdrawing fluid from the body cavity without delivering fluid into the body cavity.

32. A method of irrigating a trachea of a subject with fluid, the method comprising:
(a) moving a handle of an irrigation device to manually deliver a first volume of fluid to the trachea, without withdrawing fluid from the body cavity; and, subsequently,
(b) moving said handle to: (i) manually deliver a second volume of the fluid, and (ii) simultaneously withdrawing at least said second volume of the fluid from the trachea.

33. The method of claim 32, being executed during oral endotracheal intubation.

34. The method of claim 32, being executed during tracheotomy.

* * * * *